(12) United States Patent
Aranyi et al.

(10) Patent No.: US 8,920,438 B2
(45) Date of Patent: Dec. 30, 2014

(54) APPARATUS FOR APPLYING SURGICAL CLIPS

(75) Inventors: Ernest Aranyi, Easton, CT (US); Kenneth H. Whitfield, North Haven, CT (US); Greg Sorrentino, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 1329 days.

(21) Appl. No.: 11/245,866

(22) Filed: Oct. 7, 2005

(65) Prior Publication Data

US 2006/0079115 A1 Apr. 13, 2006

Related U.S. Application Data

(60) Provisional application No. 60/617,017, filed on Oct. 8, 2004.

(51) Int. Cl.
*A61B 17/10* (2006.01)
*A61B 17/128* (2006.01)
*A61B 17/12* (2006.01)

(52) U.S. Cl.
CPC ............ *A61B 17/1285* (2013.01); *A61B 17/12* (2013.01); *A61B 17/128* (2013.01)
USPC ........................................................ 606/142

(58) Field of Classification Search
USPC ........................................ 606/139, 142, 143
See application file for complete search history.

(56) References Cited

U.S. PATENT DOCUMENTS

| | | | |
|---|---|---|---|
| 4,242,902 A | 1/1981 | Green | |
| 4,430,997 A * | 2/1984 | DiGiovanni et al. | 606/143 |
| 4,480,640 A | 11/1984 | Becht | |
| 4,480,641 A | 11/1984 | Failla et al. | |
| 4,487,204 A | 12/1984 | Hrouda | |
| 4,491,133 A | 1/1985 | Menges et al. | |
| 4,492,232 A | 1/1985 | Green | |
| 4,500,024 A | 2/1985 | DiGiovanni et al. | |
| 4,509,518 A | 4/1985 | McGarry et al. | |
| 4,512,345 A | 4/1985 | Green | |
| 4,532,925 A | 8/1985 | Blake, III | |
| 4,534,351 A | 8/1985 | Rothfuss et al. | |

(Continued)

FOREIGN PATENT DOCUMENTS

| | | |
|---|---|---|
| DE | 20 2009 006113 | 7/2009 |
| EP | 0 085 931 A2 | 8/1983 |

(Continued)

OTHER PUBLICATIONS

European Search Report corresponding to EP 09252053; date of mailing is Dec. 1, 2009; date of completion of Search is Nov. 24, 2009 (3 Pages).

(Continued)

*Primary Examiner* — Tuan V Nguyen
*Assistant Examiner* — Son Dang

(57) ABSTRACT

A clip applying apparatus is described for applying clips seriatim to tissue. The apparatus includes a lockout member for limiting distal movement of the camming member after the proximal-most clip has been applied to tissue. In one embodiment, the apparatus includes a jaw locking member for preventing approximation of the jaw members of the apparatus. In one embodiment, a latch assembly is provided to releasably engage a clip pusher of the apparatus to the camming member of the apparatus.

12 Claims, 32 Drawing Sheets

(56) References Cited

U.S. PATENT DOCUMENTS

| | | | |
|---|---|---|---|
| 4,549,544 A | 10/1985 | Favaron | |
| 4,556,058 A | 12/1985 | Green | |
| 4,557,263 A | 12/1985 | Green | |
| 4,562,839 A | 1/1986 | Blake, III et al. | |
| 4,572,183 A | 2/1986 | Juska | |
| 4,576,165 A | 3/1986 | Green et al. | |
| 4,576,166 A | 3/1986 | Montgomery | |
| 4,590,937 A | 5/1986 | Deniega | |
| 4,598,711 A | 7/1986 | Deniega | |
| 4,602,631 A | 7/1986 | Funatsu | |
| 4,611,595 A | 9/1986 | Klieman et al. | |
| 4,612,932 A | 9/1986 | Caspar et al. | |
| 4,616,650 A | 10/1986 | Green et al. | |
| 4,616,651 A | 10/1986 | Golden | |
| 4,624,254 A | 11/1986 | McGarry et al. | |
| 4,637,395 A | 1/1987 | Caspar et al. | |
| 4,646,740 A | 3/1987 | Peters et al. | |
| 4,647,504 A | 3/1987 | Kimimura et al. | |
| 4,658,822 A | 4/1987 | Kees, Jr. | |
| 4,660,558 A | 4/1987 | Kees, Jr. | |
| 4,662,373 A | 5/1987 | Montgomery | |
| 4,662,374 A | 5/1987 | Blake, III | |
| 4,671,278 A | 6/1987 | Chin | |
| 4,674,504 A | 6/1987 | Klieman et al. | |
| 4,681,107 A | 7/1987 | Kees, Jr. | |
| 4,696,396 A | 9/1987 | Samuels | |
| 4,702,247 A | 10/1987 | Blake, III et al. | |
| 4,706,668 A | 11/1987 | Backer | |
| 4,712,549 A | 12/1987 | Peters | |
| 4,733,664 A | 3/1988 | Kirsch et al. | |
| 4,733,666 A | 3/1988 | Mercer, Jr. | |
| 4,759,364 A | 7/1988 | Boebel | |
| 4,765,335 A | 8/1988 | Schmidt et al. | |
| 4,777,949 A | 10/1988 | Perlin | |
| 4,777,950 A | 10/1988 | Kees, Jr. | |
| 4,796,625 A | 1/1989 | Kees, Jr. | |
| 4,799,481 A | 1/1989 | Transue et al. | |
| 4,821,721 A | 4/1989 | Chin et al. | |
| 4,850,355 A * | 7/1989 | Brooks et al. | 606/143 |
| 4,854,317 A | 8/1989 | Braun | |
| 4,929,239 A | 5/1990 | Braun | |
| 4,934,364 A | 6/1990 | Green | |
| 4,967,949 A | 11/1990 | Sandhaus | |
| 5,026,379 A | 6/1991 | Yoon | |
| 5,030,226 A | 7/1991 | Green et al. | |
| 5,032,127 A | 7/1991 | Frazee et al. | |
| 5,035,692 A | 7/1991 | Lyon et al. | |
| 5,047,038 A | 9/1991 | Peters et al. | |
| 5,049,152 A | 9/1991 | Simon | |
| 5,049,153 A | 9/1991 | Nakao et al. | |
| 5,084,057 A | 1/1992 | Green et al. | |
| 5,100,416 A | 3/1992 | Oh et al. | |
| 5,100,420 A | 3/1992 | Green et al. | |
| 5,104,394 A | 4/1992 | Knoepfler | |
| 5,104,395 A | 4/1992 | Thornton et al. | |
| 5,112,343 A | 5/1992 | Thornton | |
| 5,156,608 A | 10/1992 | Troidl et al. | |
| 5,163,945 A | 11/1992 | Ortiz et al. | |
| 5,171,247 A | 12/1992 | Hughett et al. | |
| 5,171,249 A | 12/1992 | Stefanchik | |
| 5,171,250 A | 12/1992 | Yoon | |
| 5,192,288 A | 3/1993 | Thompson et al. | |
| 5,197,970 A | 3/1993 | Green et al. | |
| 5,199,566 A | 4/1993 | Ortiz et al. | |
| 5,201,746 A | 4/1993 | Shichman | |
| 5,207,691 A | 5/1993 | Nardella | |
| 5,207,692 A | 5/1993 | Kraus et al. | |
| 5,246,450 A | 9/1993 | Thornton et al. | |
| 5,269,792 A | 12/1993 | Kovac et al. | |
| 5,282,807 A | 2/1994 | Knoepfler | |
| 5,282,808 A | 2/1994 | Kovac et al. | |
| 5,282,832 A | 2/1994 | Toso et al. | |
| 5,290,299 A | 3/1994 | Fain et al. | |
| 5,300,081 A | 4/1994 | Young et al. | |
| 5,304,183 A | 4/1994 | Gourlay et al. | |
| 5,306,280 A | 4/1994 | Bregen et al. | |
| 5,306,283 A | 4/1994 | Conners | |
| 5,330,442 A | 7/1994 | Green et al. | |
| 5,330,487 A | 7/1994 | Thornton et al. | |
| 5,340,360 A | 8/1994 | Stefanchik | |
| 5,354,304 A | 10/1994 | Allen | |
| 5,366,458 A | 11/1994 | Korthoff et al. | |
| 5,368,600 A | 11/1994 | Failla et al. | |
| 5,382,253 A | 1/1995 | Hogendijk | |
| 5,382,254 A | 1/1995 | McGarry | |
| 5,382,255 A | 1/1995 | Castro | |
| 5,383,881 A | 1/1995 | Green | |
| 5,395,381 A | 3/1995 | Green | |
| 5,403,327 A | 4/1995 | Thornton et al. | |
| 5,409,498 A | 4/1995 | Braddock et al. | |
| 5,413,584 A | 5/1995 | Schulze | |
| 5,423,835 A | 6/1995 | Green | |
| 5,431,667 A | 7/1995 | Thompson | |
| 5,431,668 A | 7/1995 | Burbank, III et al. | |
| 5,431,669 A | 7/1995 | Thompson | |
| 5,439,468 A | 8/1995 | Schulze et al. | |
| 5,441,509 A | 8/1995 | Vidal | |
| 5,447,513 A | 9/1995 | Davison et al. | |
| 5,449,365 A | 9/1995 | Green | |
| 5,462,555 A | 10/1995 | Bolanos | |
| 5,462,558 A | 10/1995 | Kolesa | |
| 5,474,566 A | 12/1995 | Alesi | |
| 5,474,567 A | 12/1995 | Stefanchik et al. | |
| 5,501,693 A | 3/1996 | Gravener | |
| 5,509,920 A | 4/1996 | Phillips | |
| 5,514,149 A | 5/1996 | Green | |
| 5,520,701 A | 5/1996 | Lerch | |
| 5,522,823 A | 6/1996 | Kuntz et al. | |
| 5,527,318 A | 6/1996 | McGarry | |
| 5,527,319 A | 6/1996 | Green | |
| 5,527,320 A | 6/1996 | Carruthers et al. | |
| 5,542,949 A | 8/1996 | Yoon | |
| 5,547,474 A | 8/1996 | Kloeckl | |
| 5,582,615 A | 12/1996 | Foshee et al. | |
| 5,591,178 A | 1/1997 | Green et al. | |
| 5,593,421 A | 1/1997 | Bauer | |
| 5,601,573 A | 2/1997 | Fogelberg et al. | |
| 5,601,574 A | 2/1997 | Stefanchik et al. | |
| 5,607,436 A | 3/1997 | Pratt | |
| 5,618,291 A | 4/1997 | Thompson | |
| 5,618,306 A | 4/1997 | Roth et al. | |
| 5,626,585 A | 5/1997 | Mittelstadt | |
| 5,626,586 A | 5/1997 | Pistl et al. | |
| 5,626,592 A | 5/1997 | Phillips | |
| RE35,525 E * | 6/1997 | Stefanchik et al. | 606/142 |
| 5,634,930 A | 6/1997 | Thornton et al. | |
| 5,643,291 A | 7/1997 | Pier | |
| 5,645,551 A | 7/1997 | Green | |
| 5,645,553 A | 7/1997 | Kolesa | |
| 5,649,937 A | 7/1997 | Bito et al. | |
| 5,662,676 A | 9/1997 | Koninckx | |
| 5,665,097 A | 9/1997 | Baker et al. | |
| 5,681,330 A | 10/1997 | Hughett et al. | |
| 5,695,502 A | 12/1997 | Pier | |
| 5,700,270 A * | 12/1997 | Peyser et al. | 606/142 |
| 5,700,271 A | 12/1997 | Whitfield | |
| 5,702,048 A | 12/1997 | Eberlin | |
| 5,709,706 A | 1/1998 | Kienzle et al. | |
| 5,713,911 A | 2/1998 | Racenet | |
| 5,720,756 A | 2/1998 | Green | |
| 5,725,537 A | 3/1998 | Green | |
| 5,725,538 A | 3/1998 | Green | |
| 5,725,542 A | 3/1998 | Yoon | |
| 5,755,726 A | 5/1998 | Pratt | |
| 5,769,857 A | 6/1998 | Reztzov et al. | |
| 5,772,673 A | 6/1998 | Cuny | |
| 5,779,718 A | 7/1998 | Green | |
| 5,782,844 A | 7/1998 | Yoon et al. | |
| 5,788,698 A | 8/1998 | Savornin | |
| 5,792,149 A | 8/1998 | Sherts | |
| 5,792,150 A | 8/1998 | Pratt | |
| 5,824,547 A | 10/1998 | Hashino et al. | |
| 5,824,548 A | 10/1998 | Hearn | |
| 5,827,279 A * | 10/1998 | Hughett et al. | 606/45 |

(56) References Cited

U.S. PATENT DOCUMENTS

| | | | |
|---|---|---|---|
| 5,833,695 A | 11/1998 | Yoon | |
| 5,833,696 A | 11/1998 | Whitfield | |
| 5,833,700 A * | 11/1998 | Fogelberg et al. | 606/158 |
| 5,835,199 A | 11/1998 | Phillips et al. | |
| 5,843,097 A | 12/1998 | Mayenberger et al. | |
| 5,858,018 A | 1/1999 | Shipp et al. | |
| 5,861,005 A | 1/1999 | Kontos | |
| 5,868,759 A * | 2/1999 | Peyser et al. | 606/139 |
| 5,868,761 A | 2/1999 | Nicholas | |
| 5,876,410 A | 3/1999 | Petillo | |
| 5,895,394 A | 4/1999 | Kienzle et al. | |
| 5,897,565 A | 4/1999 | Foster | |
| 5,904,693 A | 5/1999 | Dicesare | |
| 5,921,996 A | 7/1999 | Sherman | |
| 5,921,997 A * | 7/1999 | Fogelberg et al. | 606/158 |
| 5,928,251 A | 7/1999 | Aranyi | |
| 5,938,667 A * | 8/1999 | Peyser et al. | 606/142 |
| 5,951,574 A | 9/1999 | Stefanchik et al. | |
| 5,972,003 A | 10/1999 | Rousseau | |
| 5,976,159 A | 11/1999 | Bolduc et al. | |
| 5,993,465 A | 11/1999 | Shipp et al. | |
| 6,004,335 A | 12/1999 | Vaitekunas et al. | |
| 6,017,358 A | 1/2000 | Yoon et al. | |
| 6,053,908 A * | 4/2000 | Crainich et al. | 606/1 |
| RE36,720 E | 5/2000 | Green | |
| 6,059,799 A | 5/2000 | Aranyi | |
| 6,099,536 A | 8/2000 | Petillo | |
| 6,099,537 A | 8/2000 | Sugai et al. | |
| 6,139,555 A | 10/2000 | Hart et al. | |
| 6,210,418 B1 | 4/2001 | Storz et al. | |
| 6,241,740 B1 | 6/2001 | Davis | |
| 6,258,105 B1 | 7/2001 | Hart et al. | |
| 6,273,898 B1 | 8/2001 | Kienzle et al. | |
| 6,277,131 B1 | 8/2001 | Kalikow | |
| 6,306,149 B1 | 10/2001 | Meade | |
| 6,322,571 B1 | 11/2001 | Adams | |
| 6,350,269 B1 | 2/2002 | Shipp et al. | |
| 6,352,541 B1 | 3/2002 | Kienzle et al. | |
| 6,391,035 B1 | 5/2002 | Appleby et al. | |
| 6,423,079 B1 | 7/2002 | Blake, III | |
| 6,428,548 B1 | 8/2002 | Durgin et al. | |
| 6,440,144 B1 | 8/2002 | Bacher | |
| 6,461,363 B1 | 10/2002 | Gadberry et al. | |
| 6,494,886 B1 | 12/2002 | Wilk et al. | |
| 6,520,972 B2 | 2/2003 | Peters | |
| 6,527,786 B1 | 3/2003 | Davis et al. | |
| 6,537,289 B1 | 3/2003 | Kayan | |
| 6,551,333 B2 | 4/2003 | Kuhns et al. | |
| 6,569,171 B2 | 5/2003 | DeGuillebon et al. | |
| 6,599,298 B1 | 7/2003 | Forseter et al. | |
| 6,607,540 B1 | 8/2003 | Shipp | |
| 6,648,898 B1 | 11/2003 | Baxter | |
| 6,652,539 B2 | 11/2003 | Shipp et al. | |
| 6,673,083 B1 | 1/2004 | Kayan | |
| 6,679,894 B2 | 1/2004 | Damarati | |
| RE38,445 E | 2/2004 | Pistl | |
| 6,695,854 B1 | 2/2004 | Kayan | |
| 6,743,240 B2 | 6/2004 | Smith et al. | |
| 6,773,438 B1 | 8/2004 | Knodel et al. | |
| 6,776,783 B1 | 8/2004 | Frantzen et al. | |
| 6,776,784 B2 | 8/2004 | Ginn | |
| 6,780,195 B2 | 8/2004 | Porat | |
| 6,793,663 B2 | 9/2004 | Kneifel et al. | |
| 6,802,848 B2 | 10/2004 | Anderson et al. | |
| 6,814,742 B2 | 11/2004 | Kimura et al. | |
| 6,818,009 B2 | 11/2004 | Hart et al. | |
| 6,821,273 B2 | 11/2004 | Mollenauer | |
| 6,821,284 B2 | 11/2004 | Sturtz et al. | |
| 6,835,200 B2 | 12/2004 | Laufer et al. | |
| 6,837,893 B2 | 1/2005 | Miller | |
| 6,837,894 B2 | 1/2005 | Pugslery, Jr. et al. | |
| 6,837,895 B2 | 1/2005 | Mayenberger | |
| 6,840,945 B2 | 1/2005 | Mantakis et al. | |
| 6,843,794 B2 | 1/2005 | Sixto et al. | |
| 6,849,078 B2 | 2/2005 | Durgin et al. | |
| 6,849,079 B1 | 2/2005 | Blake, III et al. | |
| 6,869,435 B2 | 3/2005 | Blake, III | |
| 6,869,436 B2 | 3/2005 | Wendlandt | |
| 6,889,116 B2 | 5/2005 | Jinno | |
| 6,896,682 B1 | 5/2005 | McClellan et al. | |
| 6,911,033 B2 | 6/2005 | de Guillebon et al. | |
| 6,913,607 B2 | 7/2005 | Ainsworth et al. | |
| 6,916,327 B2 | 7/2005 | Northrup et al. | |
| 6,923,818 B2 | 8/2005 | Muramatsu et al. | |
| 6,939,356 B2 | 9/2005 | Debbas | |
| 6,942,674 B2 | 9/2005 | Belef et al. | |
| 6,942,676 B2 | 9/2005 | Buelna | |
| 6,945,978 B1 | 9/2005 | Hyde | |
| 6,945,979 B2 | 9/2005 | Kortenbach et al. | |
| 6,949,107 B2 | 9/2005 | McGuckin et al. | |
| 6,953,465 B2 | 10/2005 | Dieck et al. | |
| 6,955,643 B2 | 10/2005 | Gellman et al. | |
| 6,959,852 B2 | 11/2005 | Shelton, IV et al. | |
| 6,960,218 B2 | 11/2005 | Rennich | |
| 6,960,221 B2 | 11/2005 | Ho et al. | |
| 6,962,594 B1 | 11/2005 | Thevenet | |
| 6,963,792 B1 | 11/2005 | Green | |
| 6,964,363 B2 | 11/2005 | Wales et al. | |
| 6,964,668 B2 | 11/2005 | Modesitt et al. | |
| 6,966,875 B1 | 11/2005 | Longobardi | |
| 6,966,917 B1 | 11/2005 | Suyker et al. | |
| 6,966,919 B2 | 11/2005 | Sixto et al. | |
| 6,966,981 B2 | 11/2005 | Binder et al. | |
| 6,969,391 B1 | 11/2005 | Gazzani | |
| 6,972,023 B2 | 12/2005 | Whayne et al. | |
| 6,972,027 B2 | 12/2005 | Fallin et al. | |
| 6,973,770 B2 | 12/2005 | Schnipke et al. | |
| 6,974,446 B2 | 12/2005 | Hommann et al. | |
| 6,974,462 B2 | 12/2005 | Sater | |
| 6,974,475 B1 | 12/2005 | Wall | |
| 6,981,505 B2 | 1/2006 | Krause et al. | |
| 6,981,628 B2 | 1/2006 | Wales | |
| 6,991,597 B2 | 1/2006 | Gellman et al. | |
| 6,991,634 B2 | 1/2006 | Sugiyama et al. | |
| 6,991,635 B2 | 1/2006 | Takamoto et al. | |
| 7,052,504 B2 * | 5/2006 | Hughett | 606/142 |
| 7,211,092 B2 * | 5/2007 | Hughett | 606/142 |
| 7,316,693 B2 | 1/2008 | Viola | |
| 7,510,562 B2 | 3/2009 | Lindsay | |
| 7,637,917 B2 | 12/2009 | Whitfield | |
| 7,695,482 B2 | 4/2010 | Viola | |
| 7,717,926 B2 | 5/2010 | Whitfield | |
| 7,819,886 B2 | 10/2010 | Whitfield | |
| 7,905,890 B2 | 3/2011 | Whitfield | |
| 7,988,027 B2 | 8/2011 | Olson | |
| 8,011,550 B2 | 9/2011 | Aranyi | |
| 8,011,555 B2 | 9/2011 | Tarinelli | |
| 8,016,178 B2 | 9/2011 | Olson | |
| 8,021,375 B2 | 9/2011 | Aldrich | |
| 8,021,378 B2 | 9/2011 | Sixto, Jr. | |
| 8,056,565 B2 | 11/2011 | Zergiebel | |
| 8,070,760 B2 | 12/2011 | Fujita | |
| 8,083,668 B2 | 12/2011 | Durgin | |
| 8,088,061 B2 | 1/2012 | Wells | |
| 8,091,755 B2 | 1/2012 | Kayan | |
| 8,128,643 B2 | 3/2012 | Aranyi | |
| 8,142,451 B2 | 3/2012 | Boulnois | |
| 8,157,149 B2 | 4/2012 | Olson | |
| 8,157,151 B2 | 4/2012 | Ingmanson | |
| 8,216,257 B2 | 7/2012 | Huitema | |
| 8,236,012 B2 | 8/2012 | Molitor | |
| 8,246,634 B2 | 8/2012 | Huitema | |
| 8,246,635 B2 | 8/2012 | Huitema | |
| 8,262,679 B2 | 9/2012 | Nguyen | |
| 8,267,944 B2 | 9/2012 | Sorrentino | |
| 8,267,945 B2 | 9/2012 | Nguyen | |
| 8,267,946 B2 | 9/2012 | Whitfield | |
| 8,282,655 B2 | 10/2012 | Whitfield | |
| 8,328,822 B2 | 12/2012 | Huitema | |
| 8,336,556 B2 | 12/2012 | Zergiebel | |
| 8,348,130 B2 | 1/2013 | Shah | |
| 8,357,171 B2 | 1/2013 | Whitfield | |
| 8,371,491 B2 | 2/2013 | Huitema | |
| 8,382,773 B2 | 2/2013 | Whitfield | |

(56) References Cited

U.S. PATENT DOCUMENTS

| | | | |
|---|---|---|---|
| 8,403,945 B2 | 3/2013 | Whitfield | |
| 8,403,946 B2 | 3/2013 | Whitfield | |
| 8,409,222 B2 | 4/2013 | Whitfield | |
| 8,409,223 B2 | 4/2013 | Sorrentino | |
| 8,419,752 B2 | 4/2013 | Sorrentino | |
| 8,430,892 B2 | 4/2013 | Bindra | |
| 8,444,660 B2 | 5/2013 | Adams | |
| 8,465,502 B2 | 6/2013 | Zergiebel | |
| 8,475,473 B2 | 7/2013 | Vandenbroek | |
| 8,480,688 B2 | 7/2013 | Boulnois | |
| 8,486,091 B2 | 7/2013 | Sorrentino | |
| 8,491,608 B2 | 7/2013 | Sorrentino | |
| 8,496,673 B2 | 7/2013 | Nguyen | |
| 8,506,580 B2 | 8/2013 | Zergiebel | |
| 8,512,357 B2 | 8/2013 | Viola | |
| 8,523,882 B2 | 9/2013 | Huitema | |
| 8,529,585 B2 | 9/2013 | Jacobs | |
| 8,529,586 B2 | 9/2013 | Rosenberg | |
| 8,529,588 B2 | 9/2013 | Ahlberg | |
| 8,545,486 B2 | 10/2013 | Malkowski | |
| 8,579,918 B2 | 11/2013 | Whitfield | |
| 8,585,717 B2 | 11/2013 | Sorrentino | |
| 8,603,109 B2 | 12/2013 | Aranyi | |
| 2002/0087170 A1* | 7/2002 | Kuhns et al. | 606/143 |
| 2004/0097970 A1* | 5/2004 | Hughett | 606/142 |
| 2004/0097971 A1* | 5/2004 | Hughett | 606/142 |
| 2004/0138681 A1 | 7/2004 | Pier | |
| 2004/0193213 A1 | 9/2004 | Aranyi | |
| 2005/0119677 A1 | 6/2005 | Shipp | |
| 2005/0125010 A1 | 6/2005 | Smith et al. | |
| 2005/0149063 A1 | 7/2005 | Young et al. | |
| 2005/0171560 A1 | 8/2005 | Hughett | |
| 2005/0175703 A1 | 8/2005 | Hunter | |
| 2005/0177176 A1 | 8/2005 | Gerbi et al. | |
| 2005/0177177 A1 | 8/2005 | Viola | |
| 2005/0216036 A1 | 9/2005 | Nakao | |
| 2005/0222588 A1 | 10/2005 | Vandenbroek et al. | |
| 2005/0222590 A1 | 10/2005 | Gadberry et al. | |
| 2005/0234478 A1 | 10/2005 | Wixey et al. | |
| 2005/0256529 A1 | 11/2005 | Yawata et al. | |
| 2005/0267495 A1 | 12/2005 | Ginn et al. | |
| 2005/0277951 A1 | 12/2005 | Smith et al. | |
| 2005/0277952 A1 | 12/2005 | Arp et al. | |
| 2005/0277953 A1 | 12/2005 | Francese et al. | |
| 2005/0277954 A1 | 12/2005 | Smith et al. | |
| 2005/0277955 A1 | 12/2005 | Palmer et al. | |
| 2005/0277956 A1 | 12/2005 | Francese et al. | |
| 2005/0277958 A1 | 12/2005 | Levinson | |
| 2005/0288689 A1 | 12/2005 | Kammerer et al. | |
| 2005/0288690 A1 | 12/2005 | Bourque et al. | |
| 2006/0004388 A1 | 1/2006 | Whayne et al. | |
| 2006/0004390 A1 | 1/2006 | Rosenberg et al. | |
| 2006/0009789 A1 | 1/2006 | Gambale et al. | |
| 2006/0009790 A1 | 1/2006 | Blake, III et al. | |
| 2006/0009792 A1 | 1/2006 | Baker et al. | |
| 2006/0020270 A1 | 1/2006 | Jabba et al. | |
| 2006/0020271 A1 | 1/2006 | Stewart et al. | |
| 2006/0064117 A1 | 3/2006 | Aranyi et al. | |
| 2006/0079115 A1 | 4/2006 | Aranyi | |
| 2006/0079913 A1 | 4/2006 | Whitfield et al. | |
| 2006/0085015 A1 | 4/2006 | Whitfield et al. | |
| 2006/0190013 A1 | 8/2006 | Menn | |
| 2006/0235444 A1 | 10/2006 | Huitema et al. | |
| 2007/0118155 A1 | 5/2007 | Goldfarb et al. | |
| 2007/0288039 A1 | 12/2007 | Aranyi | |
| 2008/0243145 A1 | 10/2008 | Whitfield et al. | |
| 2010/0057105 A1 | 3/2010 | Sorrentino | |
| 2010/0057107 A1 | 3/2010 | Sorrentino | |
| 2010/0274262 A1 | 10/2010 | Schulz et al. | |
| 2011/0087242 A1 | 4/2011 | Pribanic | |
| 2011/0137323 A1 | 6/2011 | Malkowski | |
| 2011/0208212 A1 | 8/2011 | Zergiebel | |
| 2011/0224701 A1 | 9/2011 | Menn | |
| 2011/0245847 A1 | 10/2011 | Menn | |
| 2012/0029534 A1 | 2/2012 | Whitfield | |
| 2012/0109158 A1 | 5/2012 | Zammataro | |
| 2012/0116420 A1 | 5/2012 | Sorrentino | |
| 2012/0123446 A1 | 5/2012 | Aranyi | |
| 2012/0197269 A1 | 8/2012 | Zammataro | |
| 2012/0265220 A1 | 10/2012 | Menn | |
| 2012/0277765 A1 | 11/2012 | Zammataro | |
| 2012/0330326 A1 | 12/2012 | Creston | |
| 2013/0110135 A1 | 5/2013 | Whitfield | |
| 2013/0131697 A1 | 5/2013 | Hartoumbekis | |
| 2013/0165952 A1 | 6/2013 | Whitfield | |
| 2013/0172910 A1 | 7/2013 | Malkowski | |
| 2013/0172911 A1 | 7/2013 | Rockrohr | |
| 2013/0172912 A1 | 7/2013 | Whitfield | |
| 2013/0190779 A1 | 7/2013 | Whitfield | |
| 2013/0190780 A1 | 7/2013 | Whitfield | |
| 2013/0274767 A1 | 10/2013 | Sorrentino | |
| 2013/0289583 A1 | 10/2013 | Zergiebel | |
| 2013/0296891 A1 | 11/2013 | Hartoumbekis | |
| 2013/0296892 A1 | 11/2013 | Sorrentino | |
| 2013/0310849 A1 | 11/2013 | Malkowski | |
| 2013/0325040 A1 | 12/2013 | Zammataro | |
| 2014/0039526 A1 | 2/2014 | Malkowski | |
| 2014/0052157 A1 | 2/2014 | Whitfield | |
| 2014/0058412 A1 | 2/2014 | Aranyi | |

FOREIGN PATENT DOCUMENTS

| | | |
|---|---|---|
| EP | 0 086 721 | 8/1983 |
| EP | 0 324 166 A2 | 7/1989 |
| EP | 0 392 750 A1 | 10/1990 |
| EP | 0 569 223 | 11/1993 |
| EP | 0 594 003 | 4/1994 |
| EP | 0 598 529 A2 | 5/1994 |
| EP | 0 685 204 A1 | 12/1995 |
| EP | 0 732 078 A2 | 9/1996 |
| EP | 0 755 655 A | 1/1997 |
| EP | 0 769 274 | 4/1997 |
| EP | 0 769 274 A1 | 4/1997 |
| EP | 0769275 | 4/1997 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 908 423 | 4/2008 |
| EP | 1 908 423 A | 4/2008 |
| EP | 1 908 423 A2 | 4/2008 |
| EP | 1 913 881 A1 | 4/2008 |
| EP | 2 229 895 A1 | 9/2010 |
| EP | 2 332 471 | 6/2011 |
| JP | 2003033361 | 2/2003 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | WO 2006/042076 | 4/2006 |
| WO | WO 2006/042110 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A | 10/2008 |

OTHER PUBLICATIONS

Extended European Search Report corresponding to EP 10252079.8, date of mailing is Mar. 17, 2011; date of completion of Search is Mar. 8, 2011 (3 Pages).

European Search Report corresponding to EP 05810218.7, mailed on May 20, 2011; completed on Apr. 18, 2011; 3 pages.

European Search Report corresponding to EP 05807612.6, mailed on May 20, 2011; completed on May 2, 2011; 3 pages.

Extended European Search Report corresponding to EP 10251737.2, mailed on May 20, 2011; completed on May 9, 2011; 4 pages.

European Search Report corresponding to EP 09252051; date of mailing is Jan. 28, 2010; date of completion of Search is Dec. 21, 2009 (3 Pages).

(56) References Cited

OTHER PUBLICATIONS

European Search Report corresponding to EP 09252050; date of mailing is Jan. 21, 2010; date of completion of Search is Dec. 23, 2009 (3 Pages).

European Search Report corresponding to EP 09252054; date of mailing is Jan. 22, 2010; date of completion of Search is Jan. 7, 2010 (3 Pages).

Extended European Search Report corresponding to European Application No. EP 11250214.1, completed May 25, 2011; mailed Jun. 1, 2011; (3 Pages).

Extended European Search Report corresponding to EP 09252056.8, date of mailing is Feb. 5, 2010; date of completion of Search is Jan. 8, 2010 (3 Pages).

Extended European Search Report corresponding to EP 10250497.4, date of mailing is May 12, 2010; date of completion of Search is May 4, 2010 (6 Pages).

European Search Report for corresponding EP05802686 date of mailing is Jan. 18, 2012 (3 pgs).

Extended European Search Report corresponding to European Application No. EP 12 15 1313.9, completed Mar. 20, 2012 and mailed Apr. 12, 2012; (5 Pages).

Extended European Search Report corresponding to European Application No. EP 12 16 1291.5, completed Apr. 24, 2012 and mailed May 4, 2012; (5 Pages).

Extended European Search Report corresponding to European Application No. EP 12 18 6401.1, completed Nov. 22, 2012 and mailed Nov. 30, 2012; (7 Pages).

Extended European Search Report corresponding to European Application No. EP 12 18 6448.2, completed Nov. 28, 2012 and mailed Dec. 10, 2012; (6 Pages).

Extended European Search Report corresponding to European Application No. EP 12 19 1706.6, completed Dec. 19, 2012 and mailed Jan. 8, 2013; (6 Pages).

Extended European Search Report corresponding to European Application No. EP 11 25 0754.6, completed Oct. 22, 2012 and mailed Oct. 31, 2012; (6 Pages).

Extended European Search Report corresponding to European Application No. EP 12 16 2288.0, completed Jun. 4, 2012 and mailed Jul. 7, 2012; (6 Pages).

Extended European Search Report corresponding to European Application No. EP 12 16 5891.8, completed Jun. 12, 2012 and mailed Jun. 20, 2012; (6 Pages).

Extended European Search Report corresponding to European Application No. EP 12 16 4955.2, completed Aug. 23, 2012 and mailed Sep. 4, 2012; (5 Pages).

Extended European Search Report corresponding to EP 13 16 6382.5, completed Nov. 19, 2013 and mailed Nov. 28, 2013; (8 pp).

Extended European Search Report corresponding to EP 11 25 0194.5, completed Nov. 25, 2013 and mailed Dec. 3, 2013; (8 pp).

Extended European Search Report corresponding to EP 10 25 1798.4, completed Dec. 12, 2013 and mailed Jan. 2, 2014; (9 pp).

Extended European Search Report corresponding to EP 12 19 8745.7, completed Mar. 19, 2013 and mailed Apr. 11, 2013; (8 pp).

Extended European Search Report corresponding to EP 12 15 2989.5, completed Apr. 9, 2013 and mailed Apr. 18, 2013; (9 pp).

Extended European Search Report corresponding to EP 08 73 2820.9, completed Jul. 2, 2013 and mailed Jul. 9, 2013; (10 pp).

Extended European Search Report corresponding to EP 12 19 1706.6, completed Dec. 19, 2012 and mailed Jan. 8, 2013; (6 pp).

Extended European Search Report corresponding to EP 13 17 2008.8, completed Aug. 14, 2013 and mailed Aug. 28, 2013; (8 pp).

Supplementary European Search Report for EP 05802686.5-2310 date of completion is Jan. 9, 2012 (6 pages).

* cited by examiner

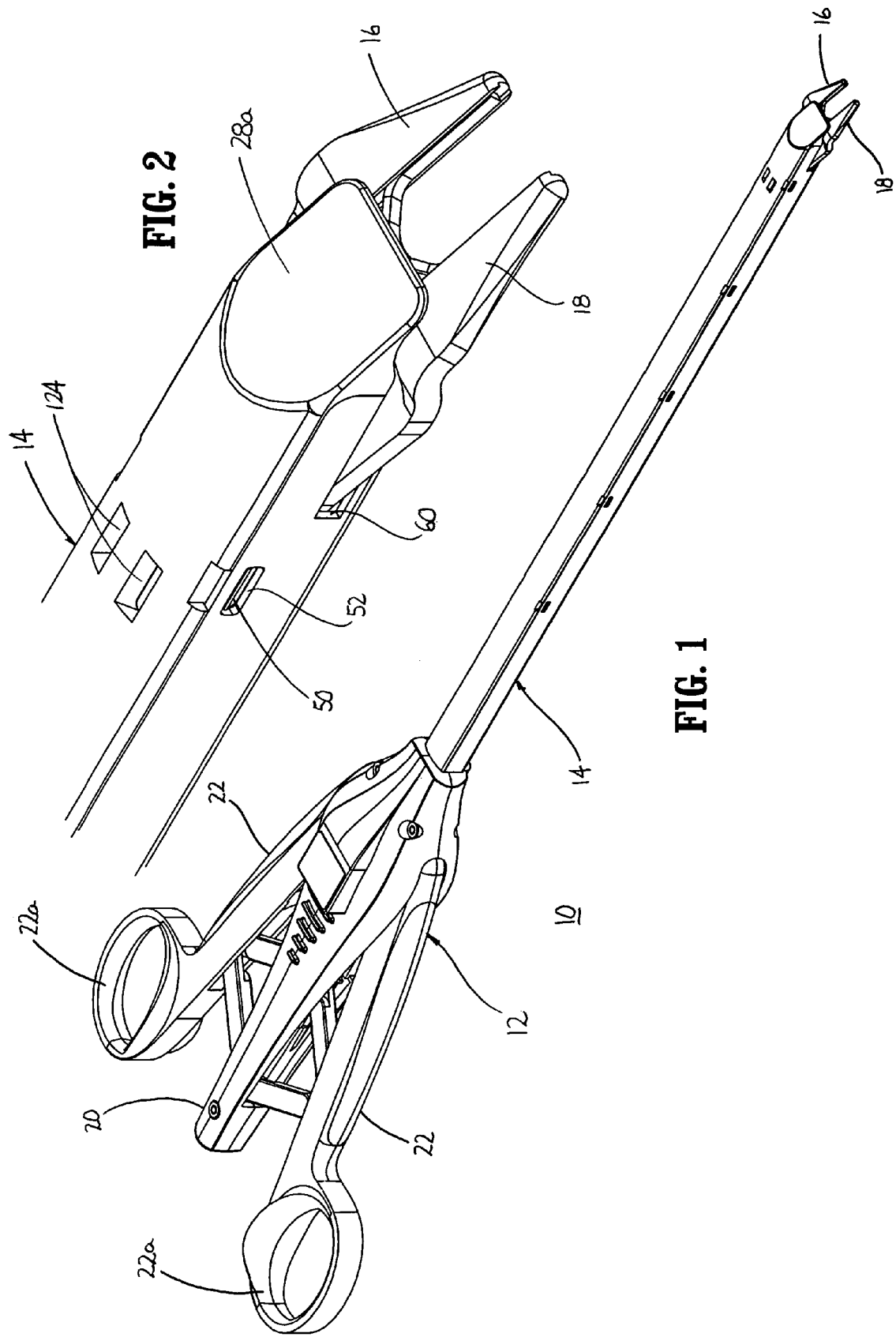

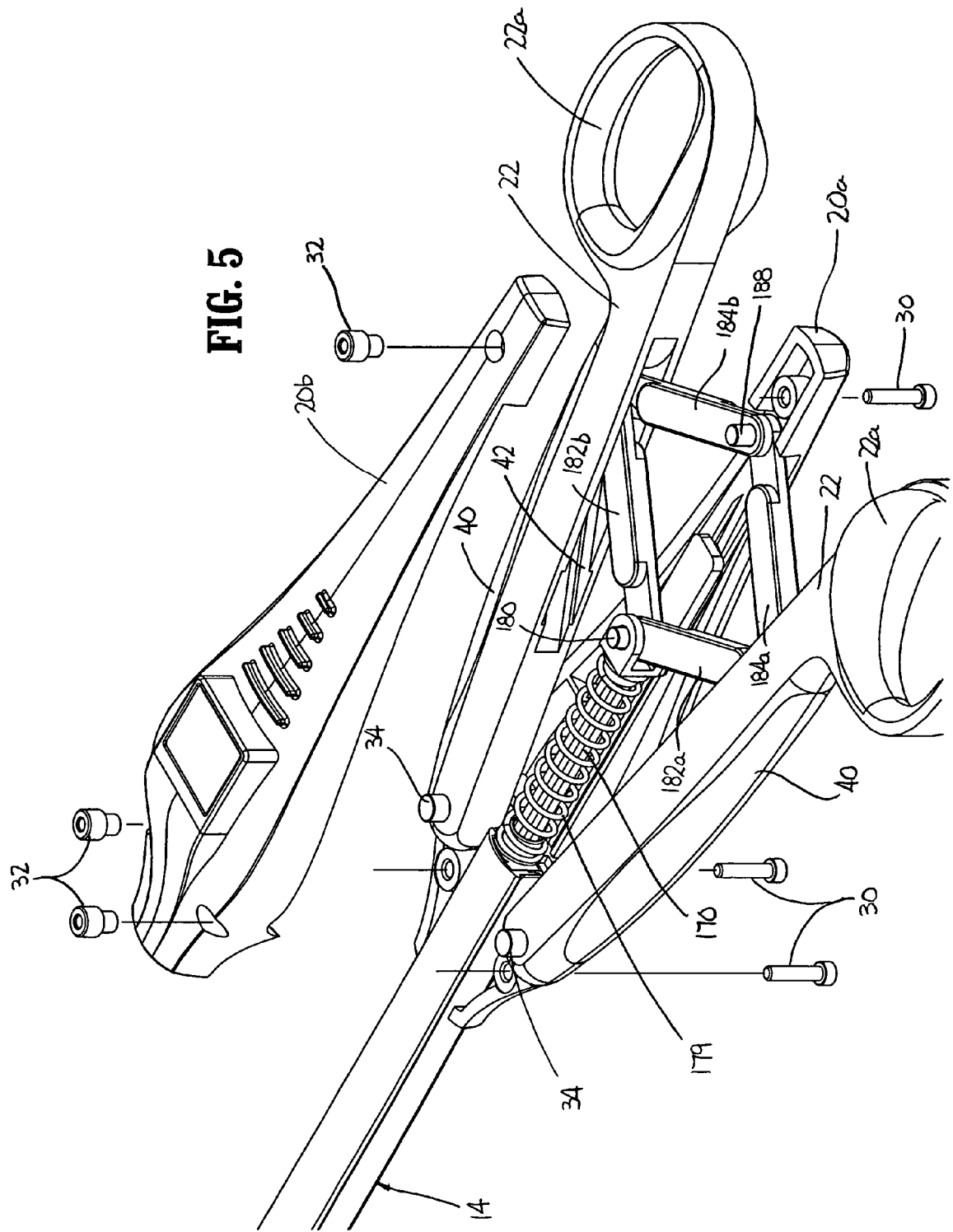

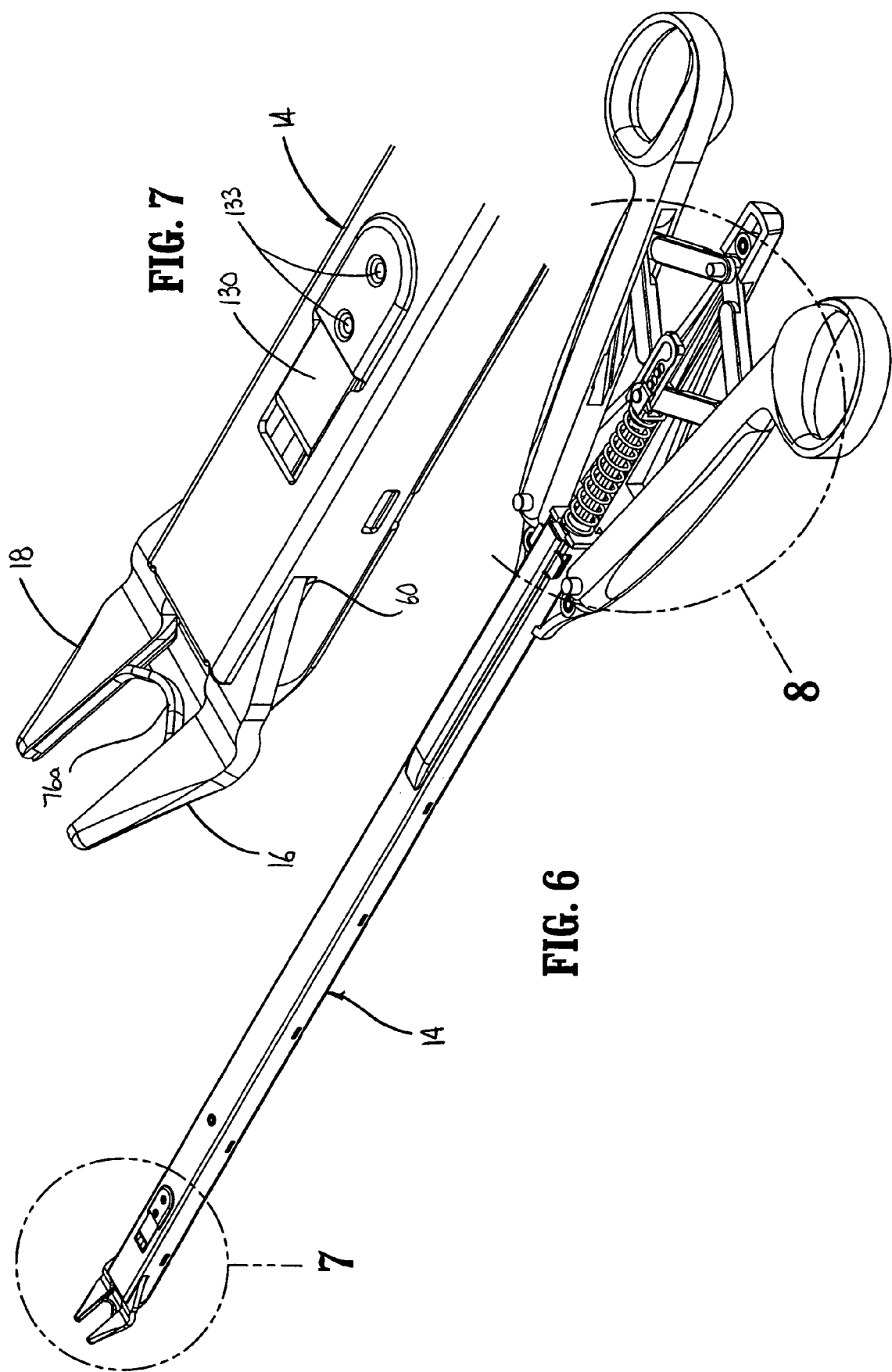

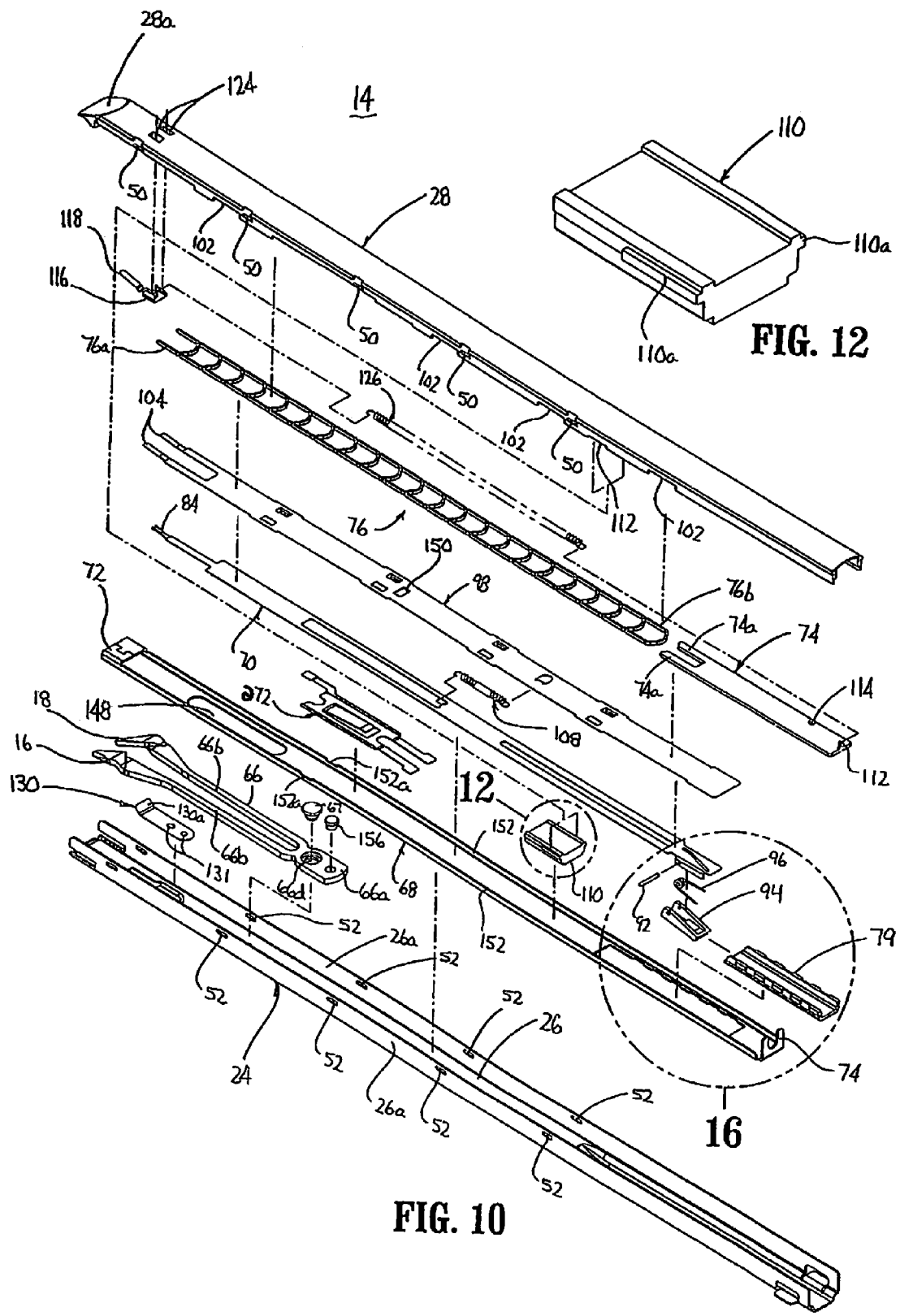

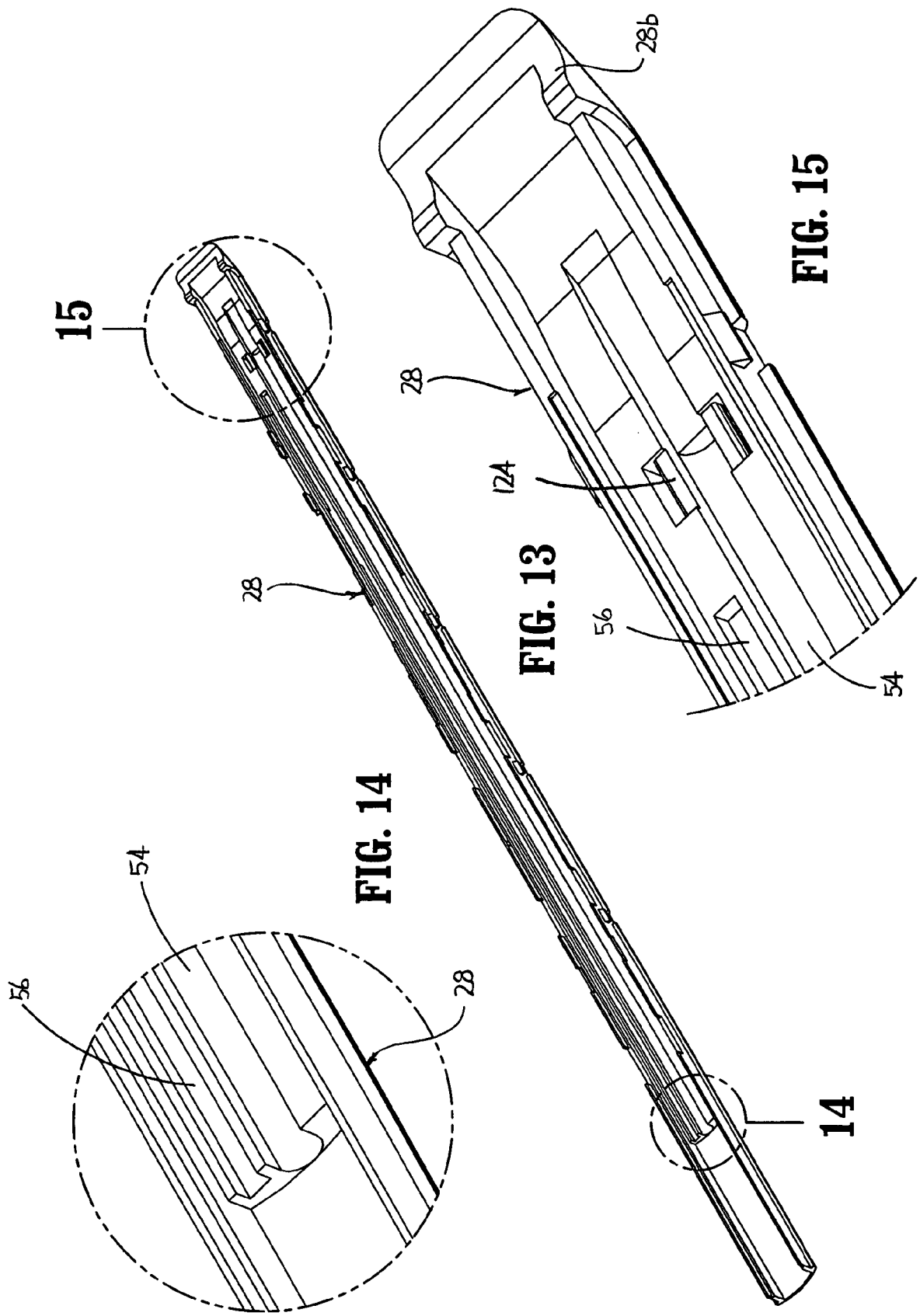

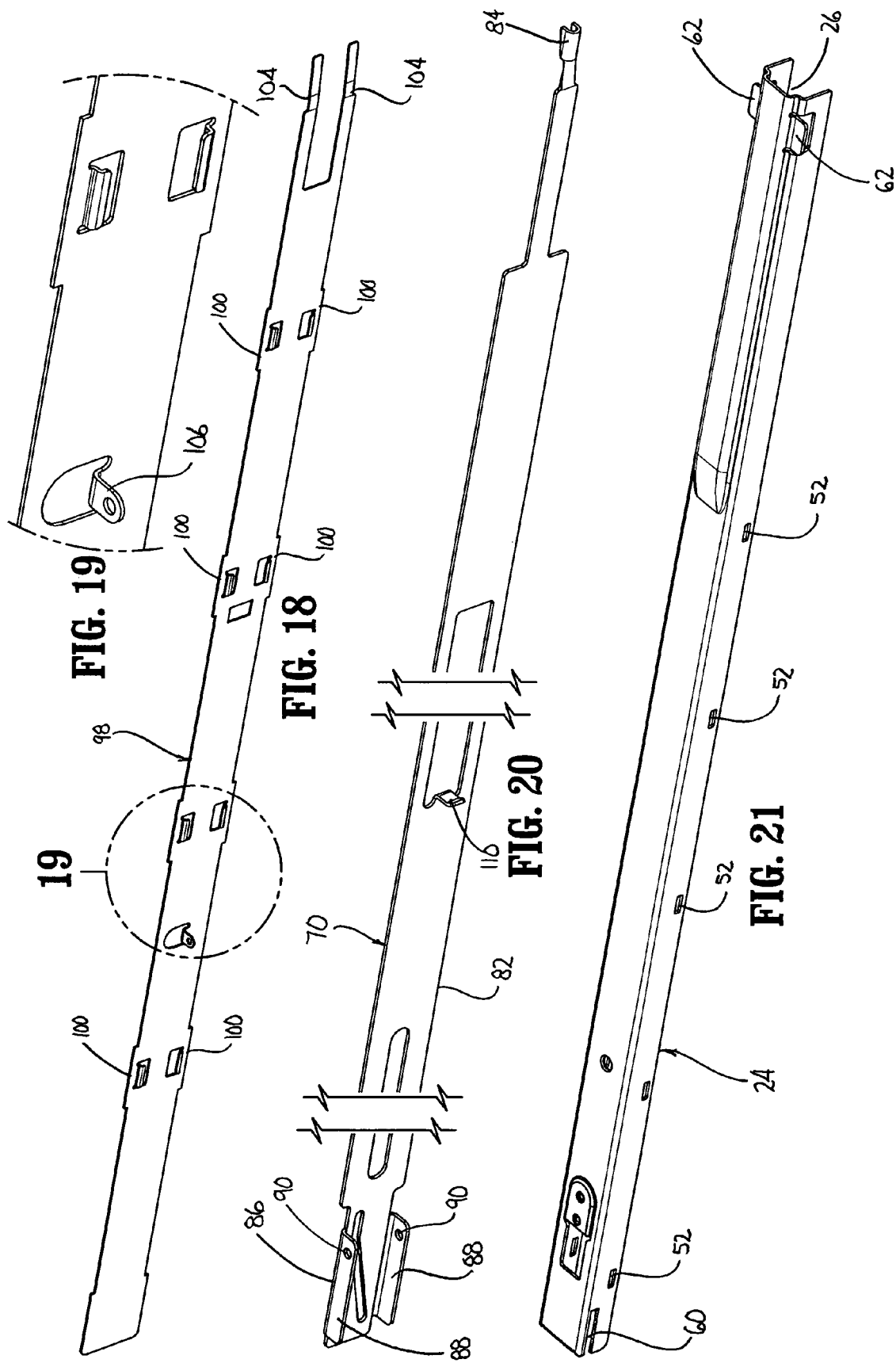

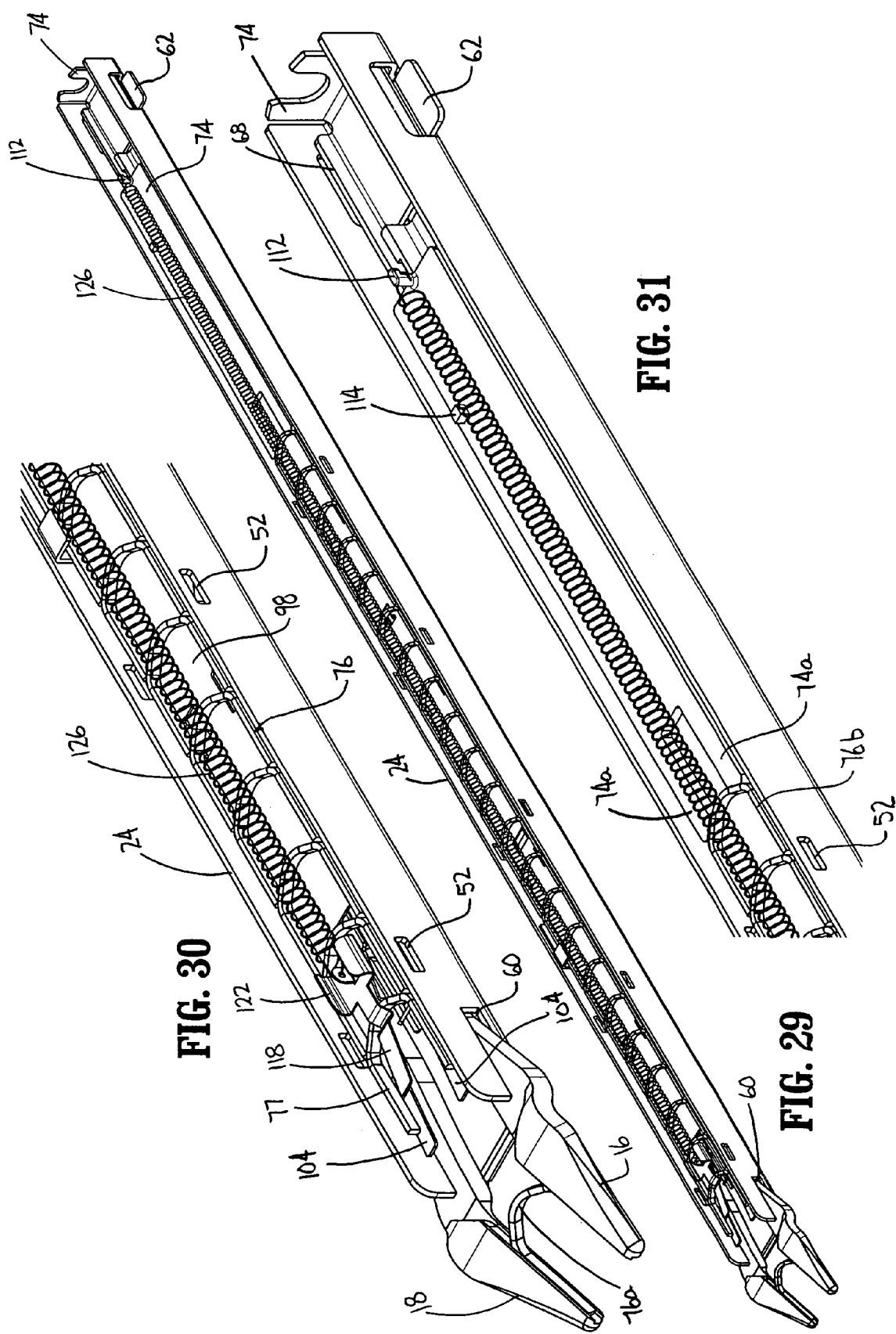

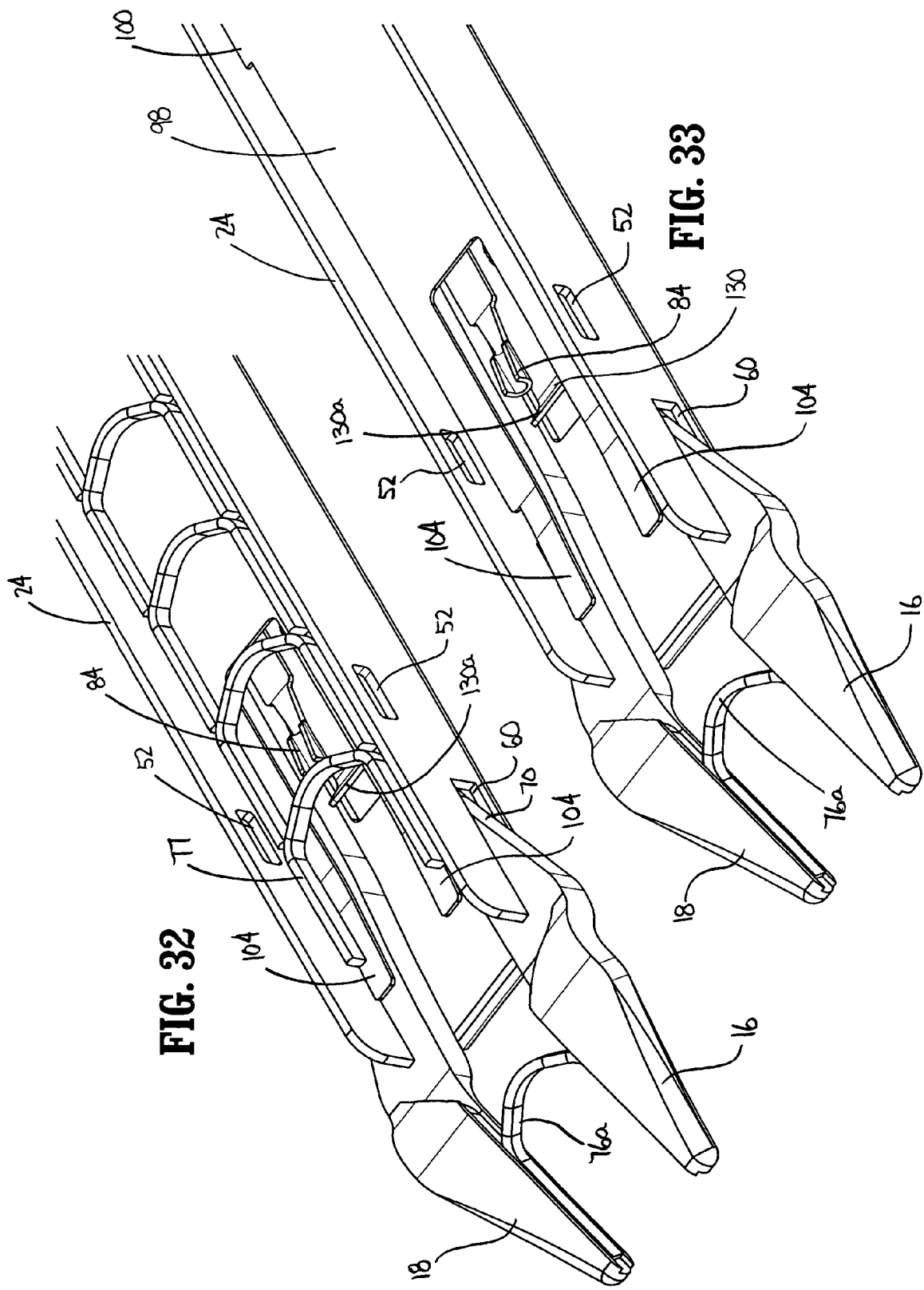

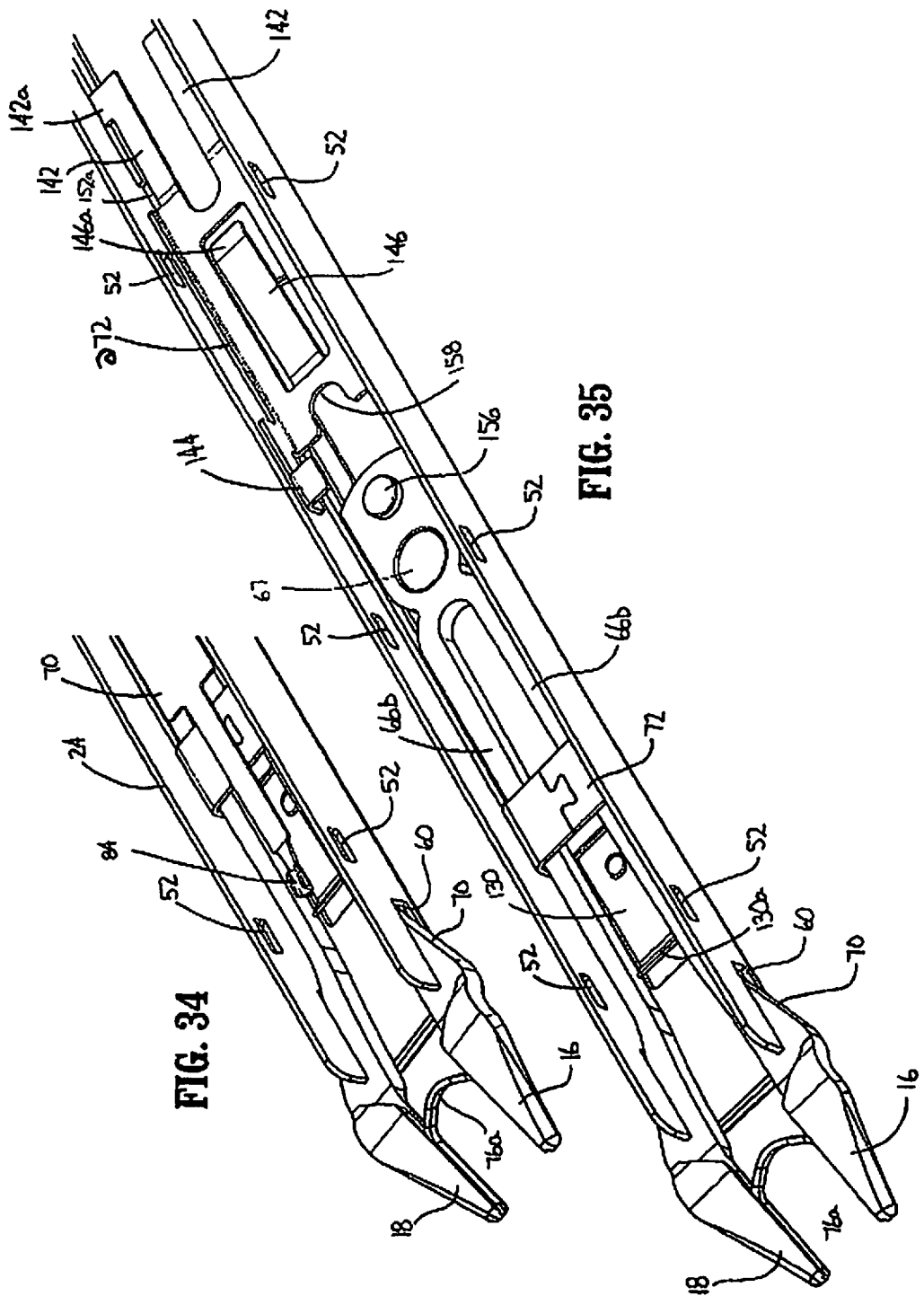

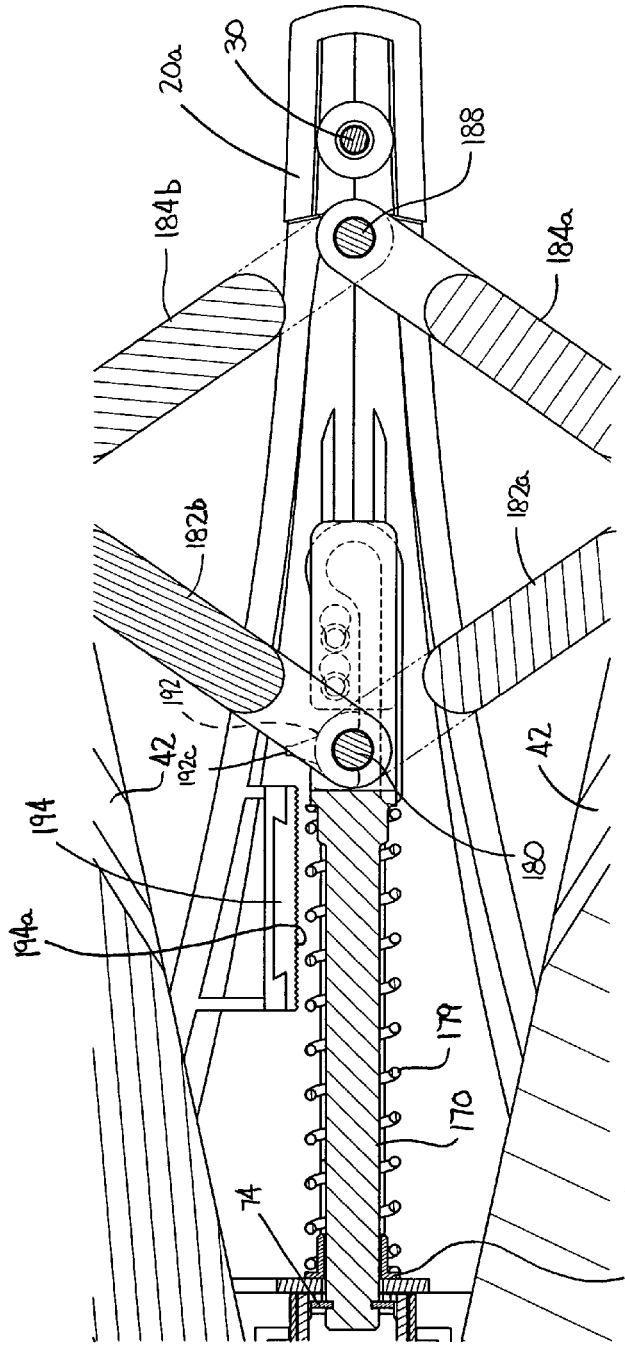
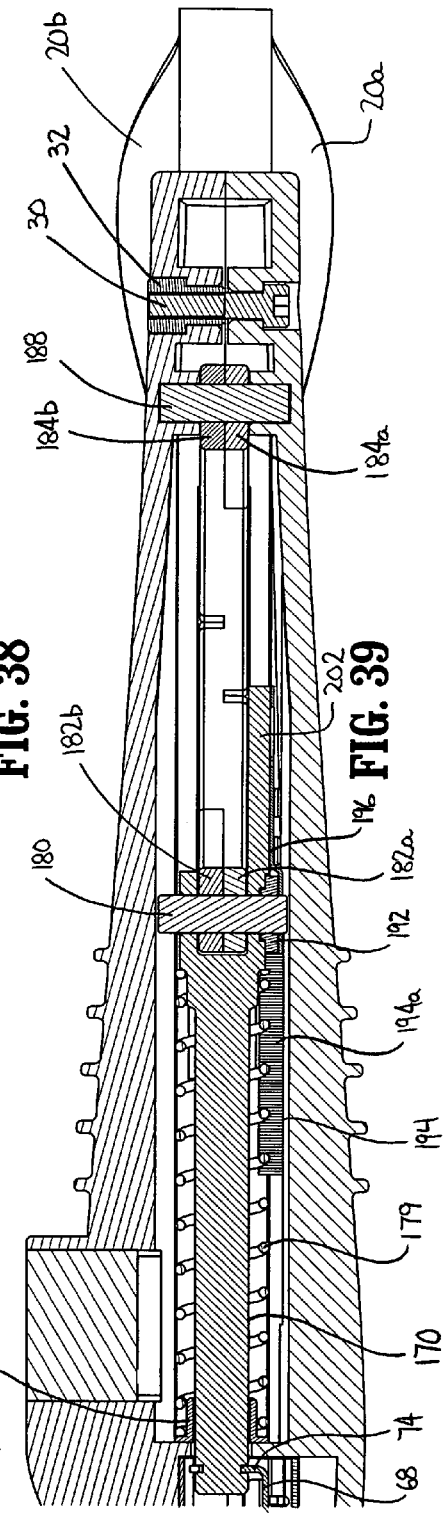
FIG. 38
FIG. 39

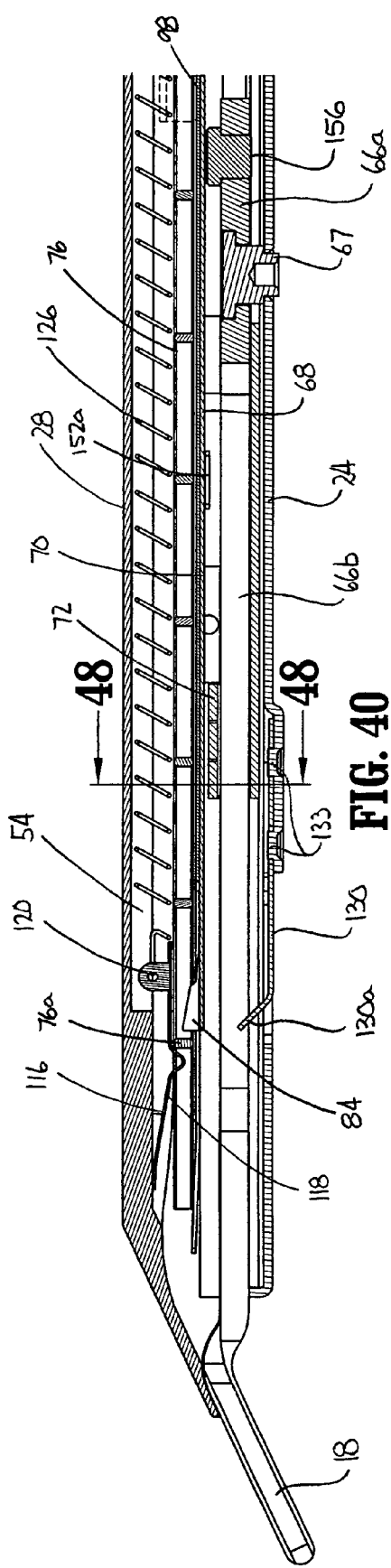

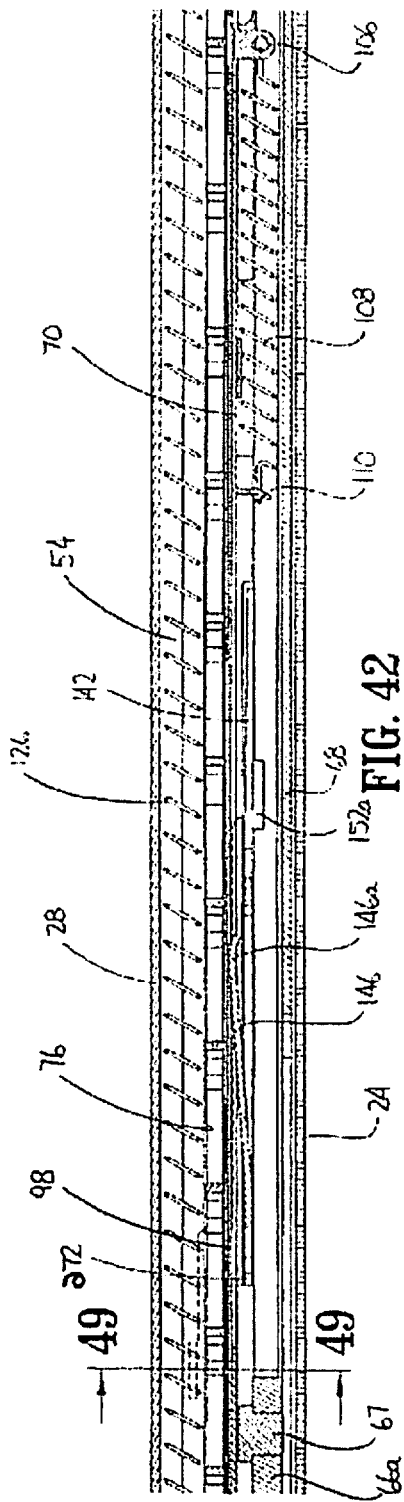
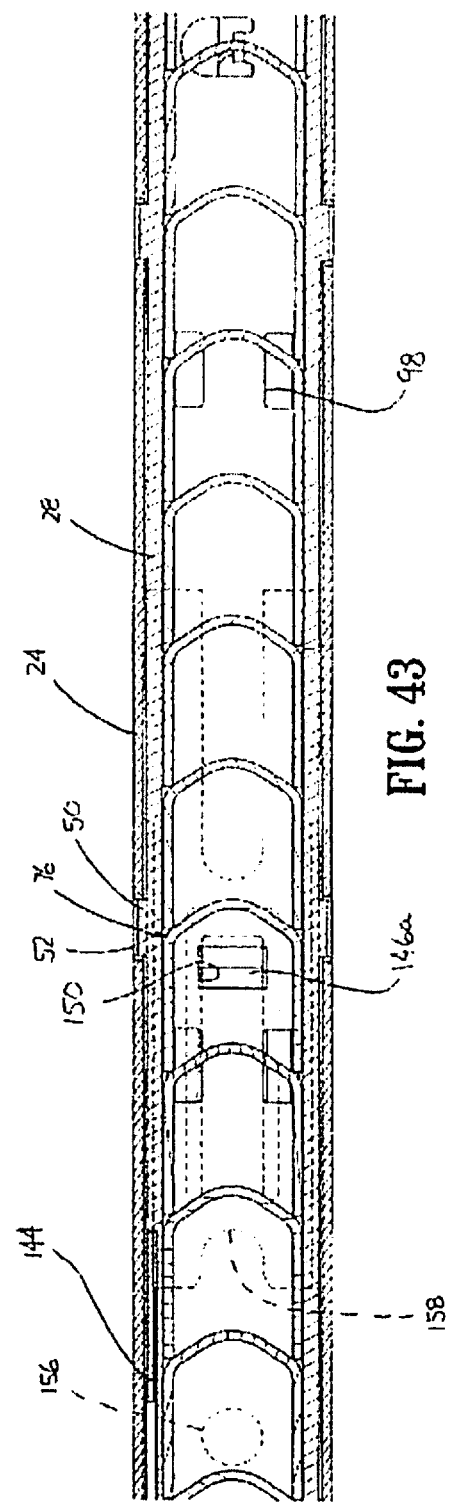
FIG. 42
FIG. 43

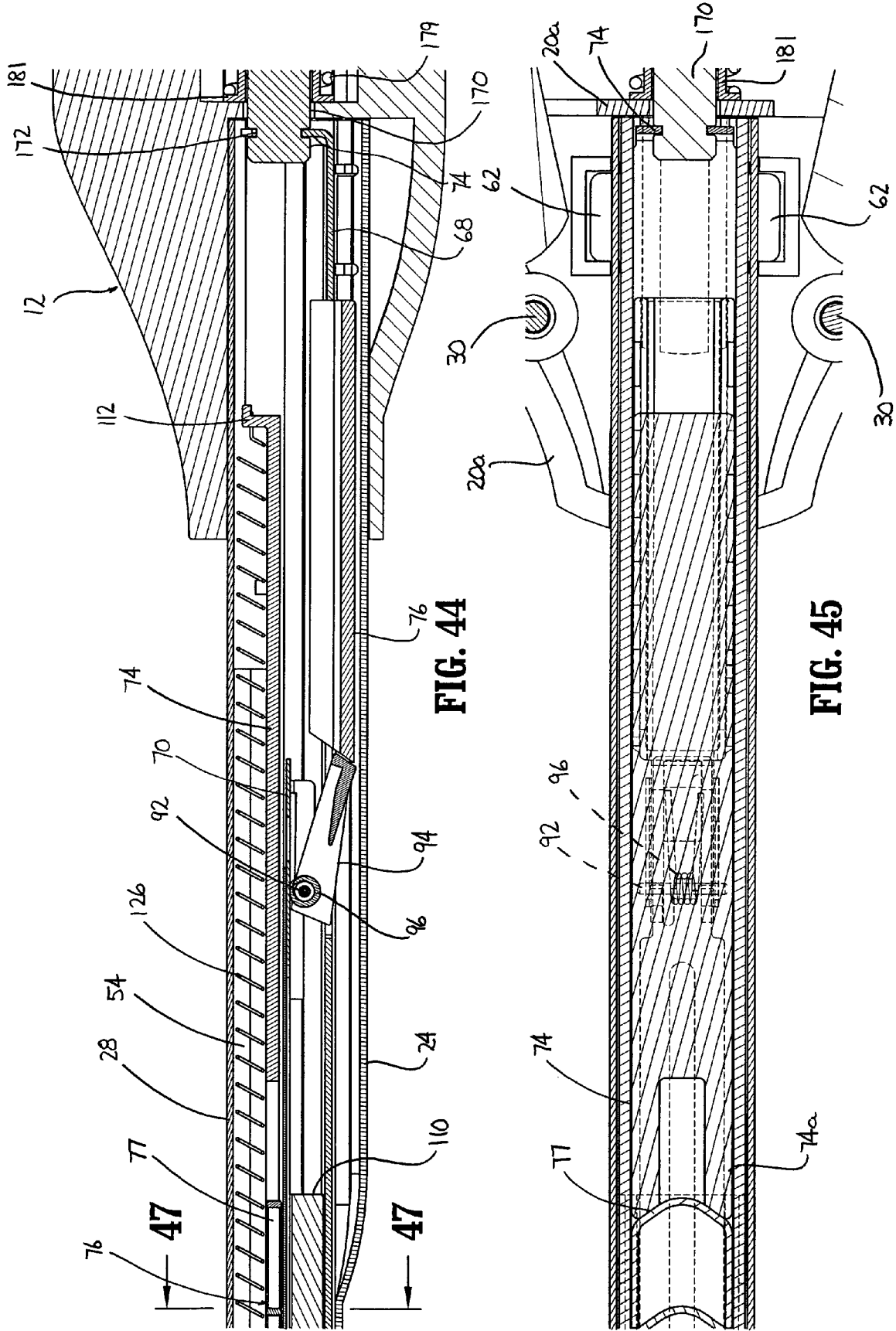

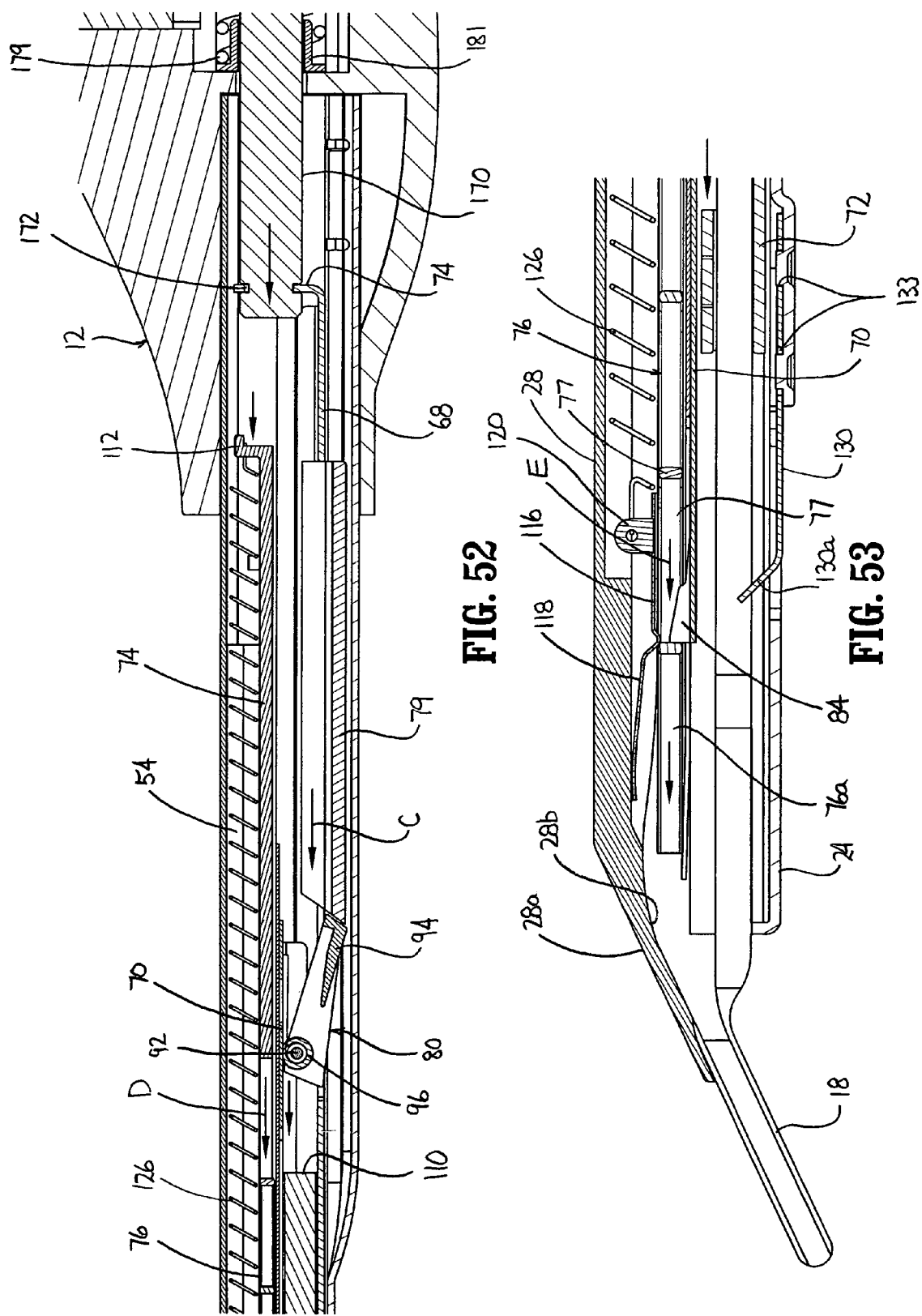

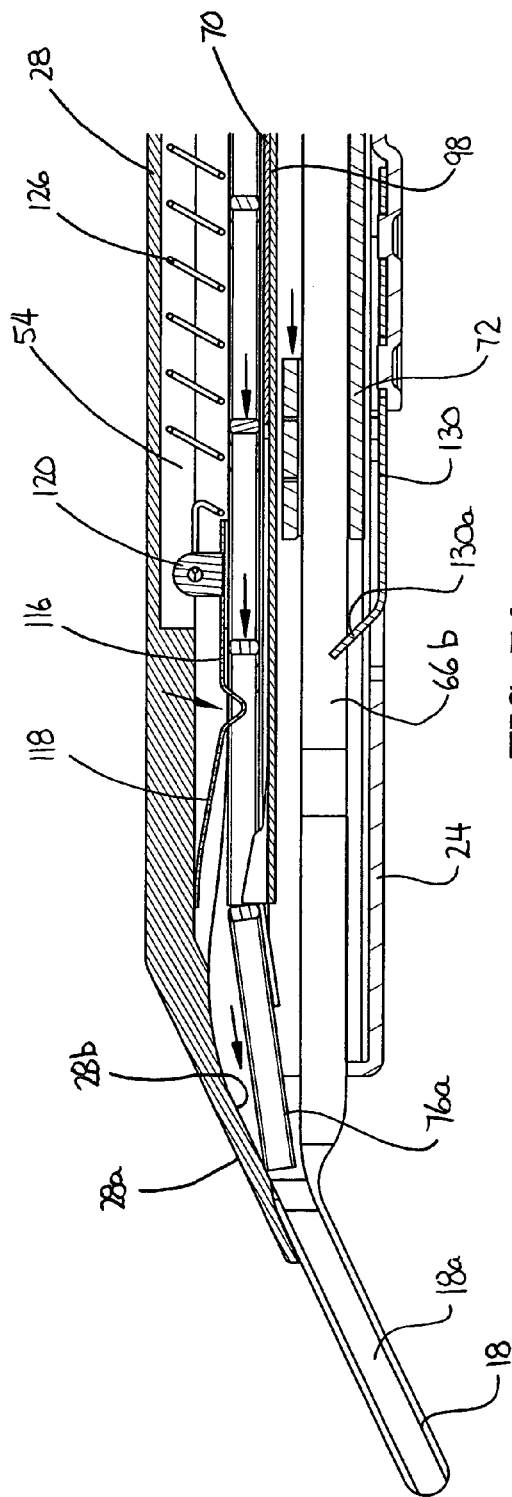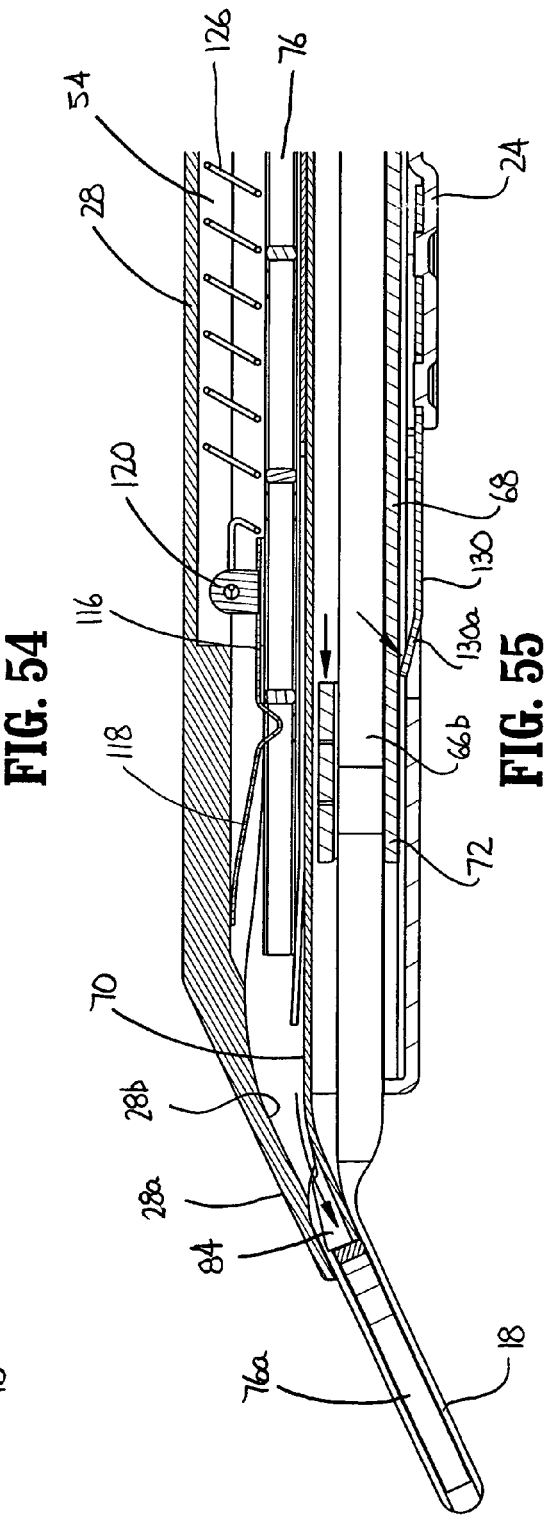
FIG. 54
FIG. 55

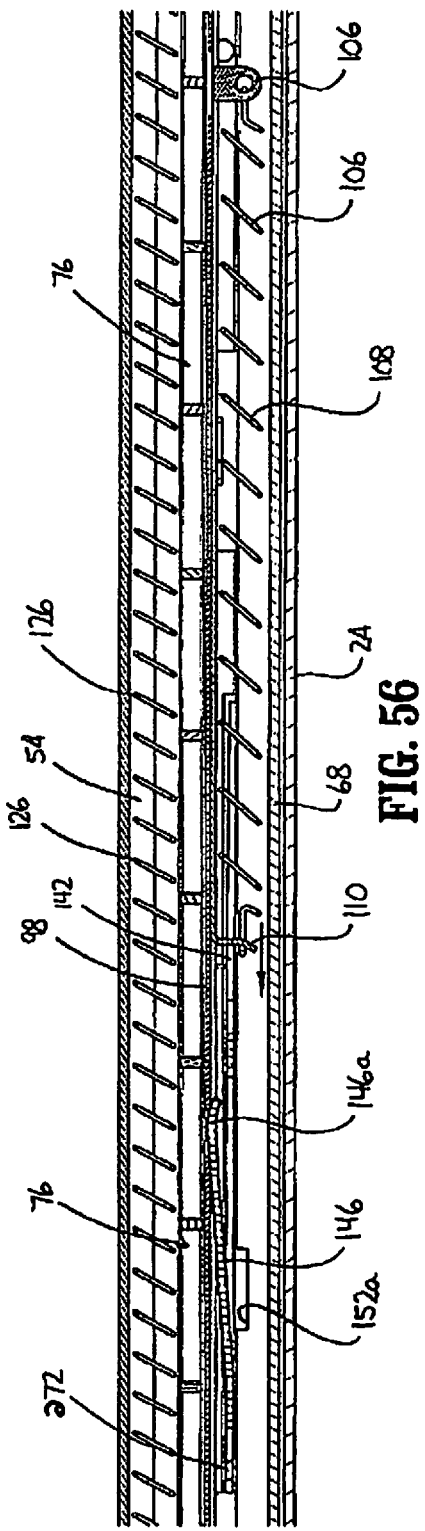
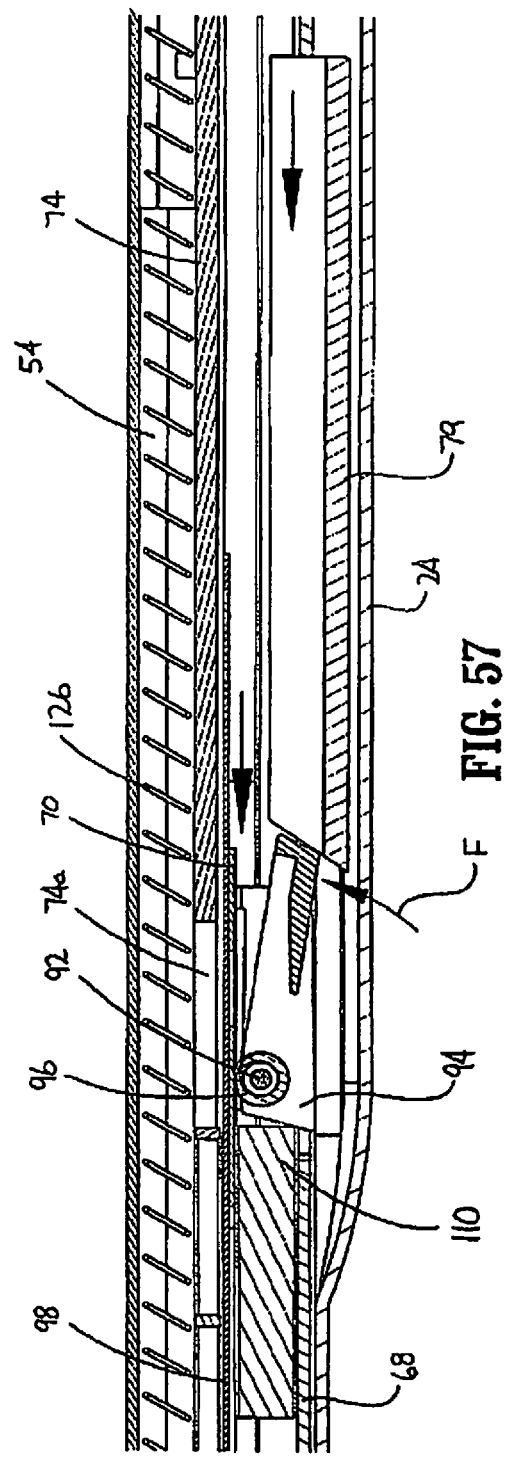
FIG. 56
FIG. 57

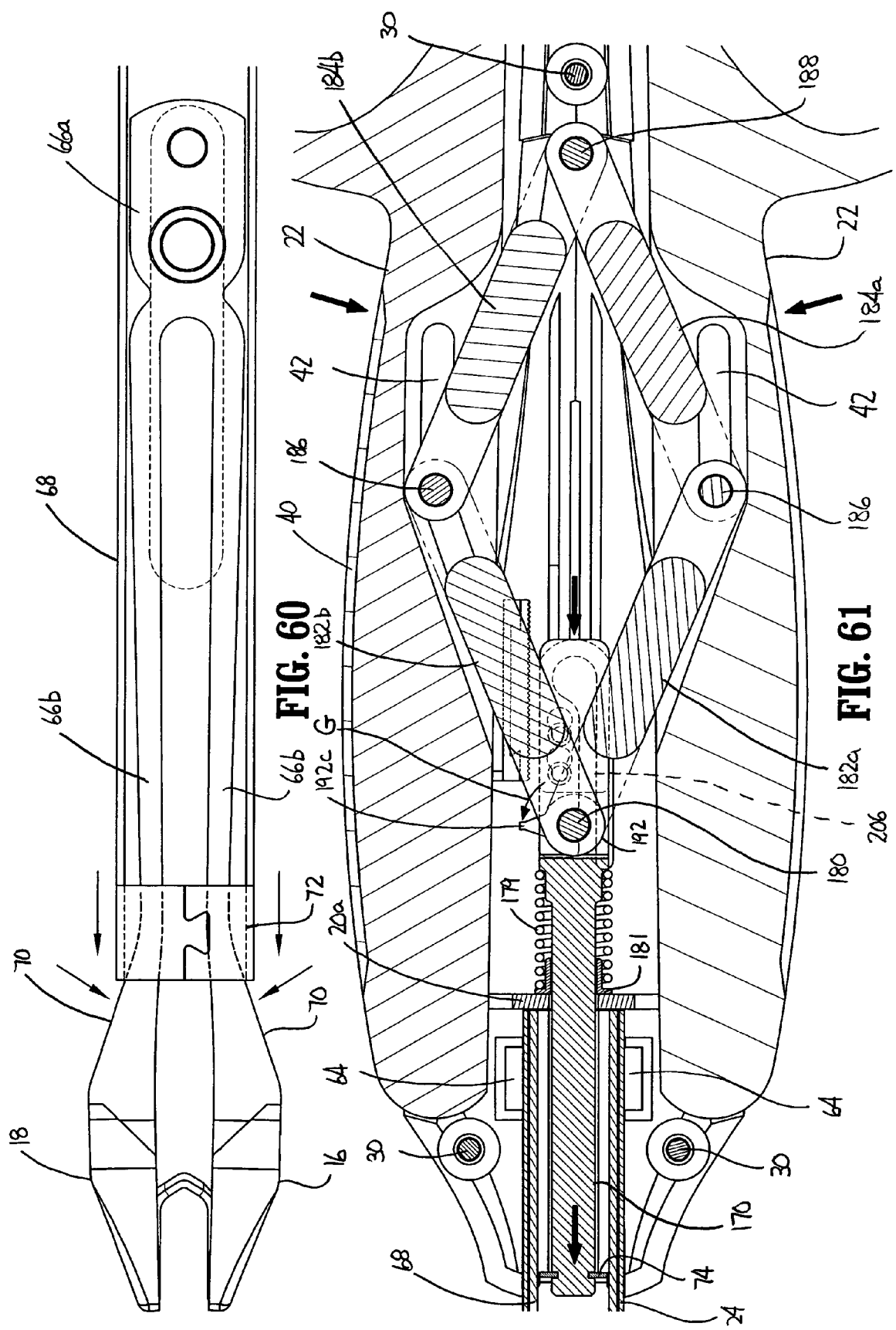

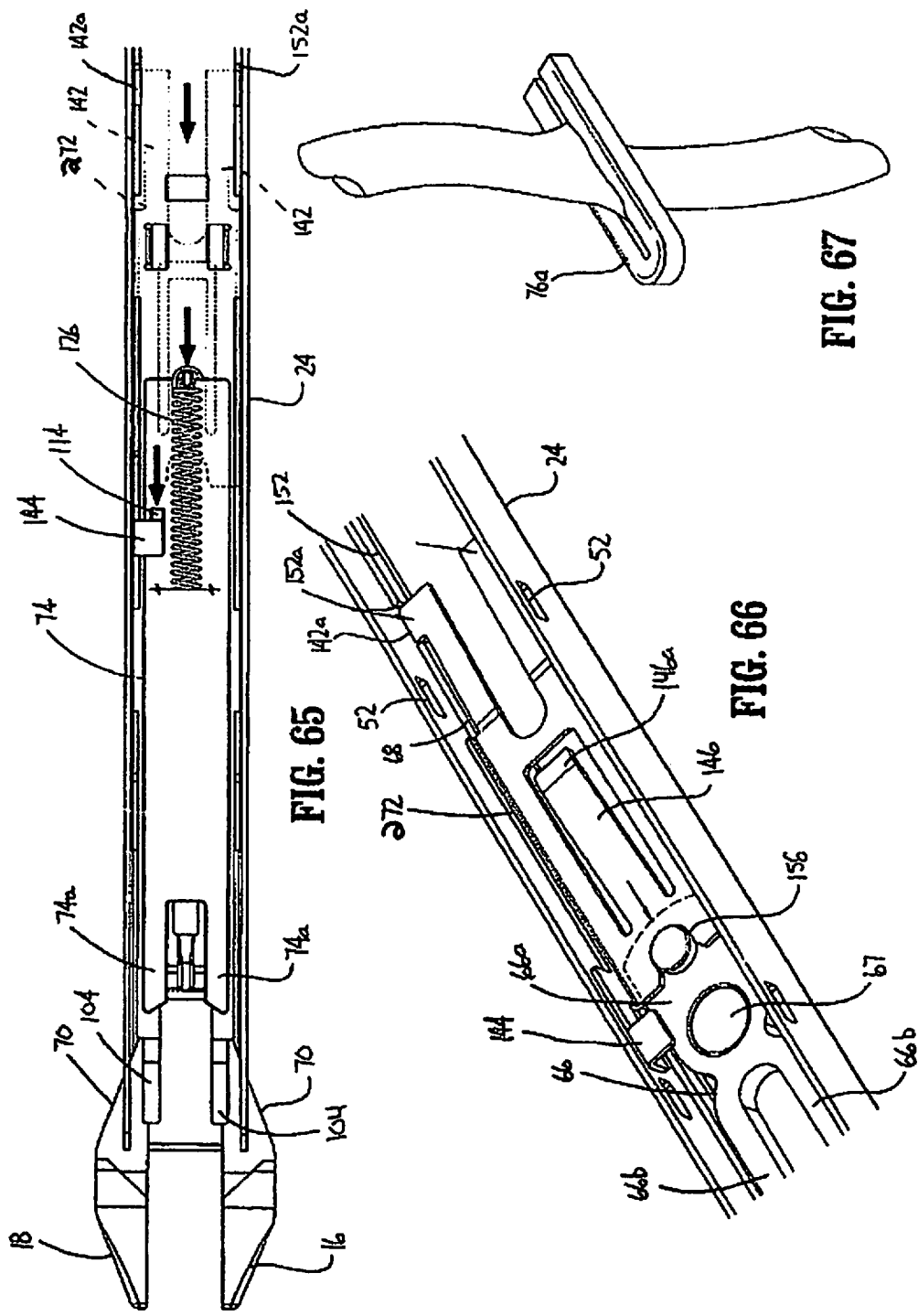

APPARATUS FOR APPLYING SURGICAL CLIPS

This application claims priority from U.S. Provisional application Ser. No. 60/617,017 filed Oct. 8, 2004, the entire contents of which are incorporated herein by reference.

BACKGROUND

1. Technical Field

This present disclosure relates generally to an apparatus for applying surgical clips to tissue. More specifically, the present disclosure relates to an apparatus for applying a series of clips to tissue seriatim.

2. Background of Related Art

Surgical procedures frequently require ligation of blood vessels, severed tissues and/or other organs to control or stop bleeding. Clip applying apparatus for quickly applying a surgical clip about tissue are well known. Such clip applying apparatus include single clip applicators and multiple clip applicators. In single clip applicators, a new clip is loaded into the apparatus after application of each clip. Multiple clip applicators include a series of clips which can be sequentially applied to tissue during the course of a surgical procedure. Because surgical procedures usually require the use of a multiplicity of surgical clips, multiple clip applicators are generally preferred.

Typically, clip applying apparatus include a handle mechanism, an elongated body portion, and a clip crimping assembly, e.g., a jaw or pair of jaws. Such clip applying apparatus are configured for endoscopic or open surgical procedures. Although known clip applying apparatus for sequentially advancing individual clips have provided good results, a continuing need exists for a clip applying apparatus which is less complex and provides effective hemostasis.

SUMMARY

In accordance with the present disclosure, an apparatus for applying surgical clips is provided which includes a handle portion including a housing and at least one movable handle and a body portion housing a clip stack. A pair of jaws is supported at the distal end of the body portion. The body portion includes a clip pusher, a camming member and a clip follower. The clip pusher is movably positioned within the body portion and is operable to advance a distal-most clip from the clip stack to a position between the pair of jaws. The camming member is movably positioned within the body portion and is operable to approximate or move the pair of jaws toward each other to deform the distal-most clip of the clip stack. The clip follower is positioned proximally of the clip stack and is operable to urge the clip stack distally towards the pair of jaws. In one embodiment, the body portion includes a lockout member and a stop member. The lockout member is movable from a first position in slidable relation to the camming member to a second position interlocked with the camming member. In its second position, the lockout member is positioned to abut the stop member to limit distal movement of the camming member.

In one embodiment, the lockout member includes at least one flexible leg having a projection and the camming member includes at least one slot dimensioned to receive the projection to interlock or secure the lockout member to the camming member. The at least one flexible leg can include a pair of flexible legs and the at least one slot can include a pair of slots. The lockout member can include a resilient finger which is positioned to releasably retain the lockout member in its first position. In one embodiment, the body portion further includes a separator plate which includes an opening dimensioned to receive a portion of the resilient finger of the lockout member to retain the lockout member in its first position. The clip follower may include a tab and the lockout member may include an engagement member such that the tab is movable into the engagement member to move the lockout member from its first position to its second position. In one embodiment, the tab is positioned to engage the engagement member after the proximal most clip has been advanced to the pair of jaws. Alternately, the tab can be positioned to engage the engagement member when one or more clips are remaining in the apparatus.

In one embodiment, an apparatus for applying surgical clips is provided which includes a handle portion having at least one movable handle and a body portion including a clip pusher and a camming member. The clip pusher is movably supported within the body portion to advance a distal-most clip of a clip stack to a position between a pair of jaws supported at a distal end of the body portion. The camming member is movably supported within the body portion from a retracted position to an advanced position to approximate the pair of jaws. A latch assembly is supported on the clip pusher and includes a pivotal latch member which is movable from a first position engaged with an abutment supported on the camming member to a second position disengaged from the abutment of the camming member. The camming member is operably connected to the at least one movable handle such that movement of the at least one movable handle through an actuation stroke effects movement of the camming member from its advanced position to its retracted position. In one embodiment, the pivotal latch member is urged towards its first position by a biasing member such that movement of the camming member from its retracted position to its advanced position initially effects advancement of the clip pusher. A latch cam is fixedly supported on the body portion and is positioned to engage the pivotal latch member after the clip pusher has advanced the distal-most clip of the clip stack to its position between the jaws to disengage the latch member from the abutment. In one embodiment, a biasing member is positioned to urge the clip pusher to a retracted position after the latch member is disengaged from the abutment. In one embodiment, the body portion includes a housing body and a housing cover and the latch cam is supported on the housing cover. The handle portion can include a yoke which is connected to a proximal end of the camming member. In one embodiment, the at least one handle is operably connected to the yoke by at least one front link such that movement of the at least one handle through an actuation stroke effects advancement of the yoke and the camming member. The handle portion can include a pair of handles with each handle operably connected to the yoke by one front link. In one embodiment, a pair of rear links are provided. Each of the rear links has a first end pivotally connected to a respective front link by a first pivot member and a second end pivotally connected to the handle portion by a second pivot member. Each of the pair of handles defines a cam channel for slidably receiving a respective one of the first pivot members.

In one embodiment, an apparatus for applying surgical clips includes a handle portion, a body portion extending distally from the handle portion, and a jaw body supported at a distal end of the body portion. The jaw body includes first and second jaws movable from a spaced position to a more approximated position. In one embodiment, the body portion includes a camming member which is movable from a retracted position to an advanced position to effect movement of the first and second jaws from their spaced position to their more approximated position. The body portion further includes a resilient jaw locking member removably positioned between the first and second jaws to prevent the jaws from moving from their spaced position to their more approximated position. In one embodiment, the jaw locking member is in the form of a resilient plate and the jaw body includes a pair of inwardly deformable legs. Each of the legs supports one of the first and second jaws and the locking member being positioned between the legs of the jaw body. A distal end of the camming is slidably positioned about the legs of the jaw body and is movable from its retracted position to its advanced position to move the locking member from between the legs of the jaw body and subsequently to effect movement of the first and second jaws to their more approximated position.

BRIEF DESCRIPTION OF THE DRAWINGS

Various embodiments of the presently disclosed clip applying apparatus are described herein with reference to the drawings, wherein:

FIG. 1 is a perspective view of one embodiment of the presently disclosed clip applying apparatus;

FIG. 2 is an enlarged perspective view of the distal end of the clip applying apparatus shown in FIG. 1;

FIG. 5 is a perspective view of the proximal portion of the clip applying apparatus shown in FIG. 4 with the top housing half-section exploded;

FIG. 6 is a perspective view of the clip applying apparatus shown in FIG. 1 with the top housing half-section removed;

FIG. 7 is an enlarged view of the indicated area of detail shown in FIG. 6;

FIG. 10 is an exploded view of the body portion of the clip applying apparatus shown in FIG. 1;

FIG. 12 is an enlarged view of the indicated area of detail shown in FIG. 12;

FIG. 13 is a bottom perspective view of the housing cover of the clip applying apparatus shown in FIG. 1;

FIG. 14 is an enlarged view of the indicated area of detail shown in FIG. 13;

FIG. 15 is an enlarged view of the indicated area of detail shown in FIG. 13;

FIG. 18 is a bottom perspective view of the separator plate of the clip applying apparatus shown in FIG. 1;

FIG. 19 is an enlarged view of the indicated area of detail shown in FIG. 18;

FIG. 20 is a bottom perspective view of the clip pusher of the clip applying apparatus shown in FIG. 1;

FIG. 21 is a bottom perspective view of the housing body of the clip applying apparatus shown in FIG. 1;

FIG. 29 is a perspective view of the body portion of the clip applying apparatus shown in FIG. 1 with the housing cover removed;

FIG. 30 is an enlarged perspective view of the distal end of the body portion shown in FIG. 29;

FIG. 31 is an enlarged perspective view of the proximal end of the body portion shown in FIG. 29;

FIG. 32 is an enlarged perspective view of the distal end of the body portion shown in FIG. 29 with the clip follower biasing member and the clip stop member removed;

FIG. 33 is an enlarged perspective view of the distal end of the body portion shown in FIG. 32 with the clip stack removed;

FIG. 34 is an enlarged perspective view of the distal end of the body portion shown in FIG. 33 with the separator plate shown removed;

FIG. 35 is an enlarged perspective view of the distal end of the body portion shown in FIG. 34 with the clip pusher removed;

FIG. 38 is an enlarged view of the indicated area of detail shown in FIG. 36;

FIG. 39 is an enlarged view of the indicated area of detail shown in FIG. 37;

FIG. 40 is an enlarged view of the indicated area of detail shown in FIG. 37;

FIG. 41 is an enlarged view of the indicated area of detail shown in FIG. 36;

FIG. 42 is an enlarged view of the indicated area of detail shown in FIG. 37;

FIG. 43 is an enlarged view of the indicated area of detail shown in FIG. 36;

FIG. 44 is an enlarged view of the indicated area of detail shown in FIG. 37;

FIG. 45 is an enlarged view of the indicated area of detail shown in FIG. 36;

FIG. 52 is a side cross-sectional view of the proximal portion of the body portion of the clip applying apparatus shown in FIG. 1 during initial actuation of the handle portion.

FIG. 53 is a side cross-sectional view of the distal end of the body portion of the clip applying apparatus shown in FIG. 1 during initial actuation of the handle portion;

FIG. 54 is a side cross-sectional view of the distal end of the body portion of the clip applying apparatus shown in FIG. 1 during further actuation of the handle portion;

FIG. 55 is a side cross-sectional view of the distal end of the body portion of the clip applying apparatus shown in FIG. 1 during further actuation of the handle portion;

FIG. 56 is a side cross-sectional view of the body portion shown in FIG. 42 after further actuation of the handle portion;

FIG. 57 is a side cross-sectional view of the body portion shown in FIG. 44 after further actuation of the handle portion;

FIG. 60 is a top view of the jaw body and camming member shown in FIG. 46 with the camming member advanced further distally;

FIG. 61 is a top cross-sectional view of the handle portion shown in FIG. 51 with the handle portion after further actuation of the handle portion;

FIG. 65 is a top view of the distal portion of the body portion of the clip applying apparatus shown in FIG. 36 illustrating the lockout tab of the clip follower engaging the engagement member of the lockout;

FIG. 66 is top perspective view of a portion of the body portion of the clip applying apparatus shown in FIG. 36 illustrating the lockout engaging the stop member; and FIG. 67 is a perspective view of a clip of the clip stack of the clip applying apparatus shown in FIG. 36 deformed about tissue.

DETAILED DESCRIPTION OF EMBODIMENTS

Figure 3:
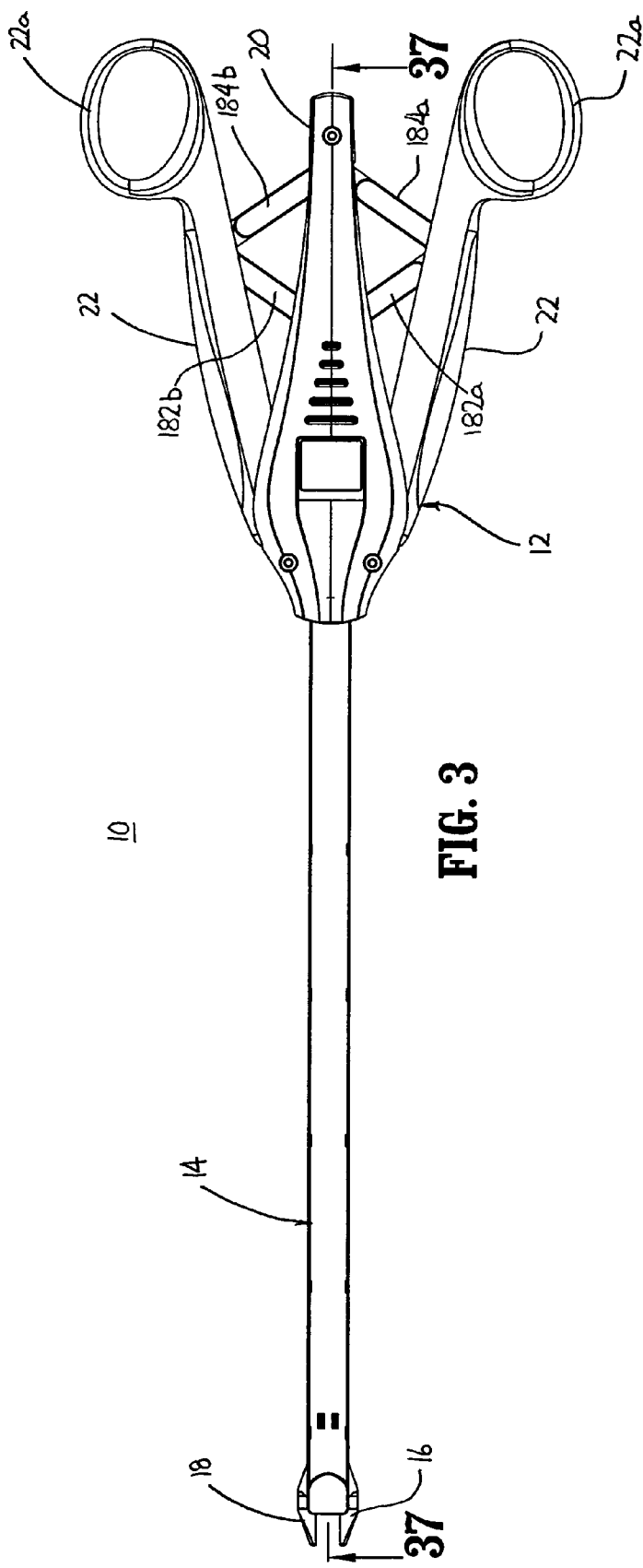
FIG. 3 is a top view of the clip applying apparatus shown in FIG. 1.
Figure 4:
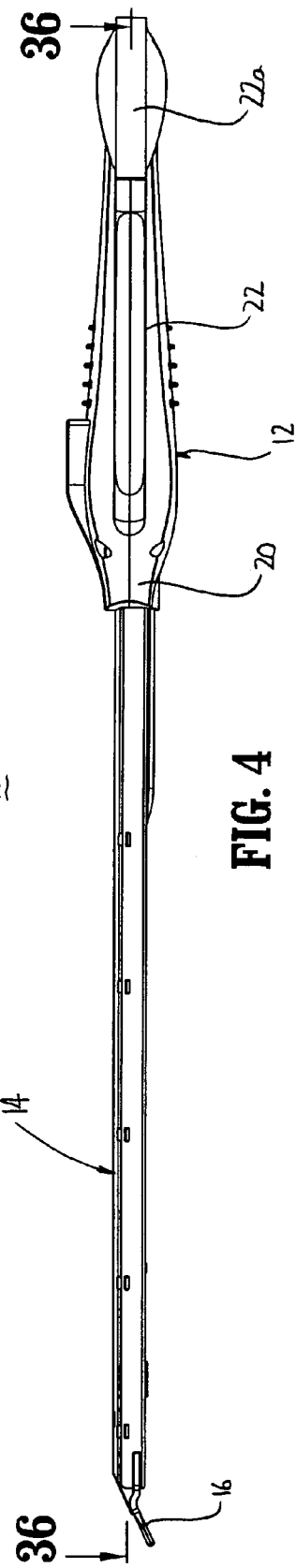
FIG. 4 is a side view of the clip applying apparatus shown in FIG. 1.
Figure 8:
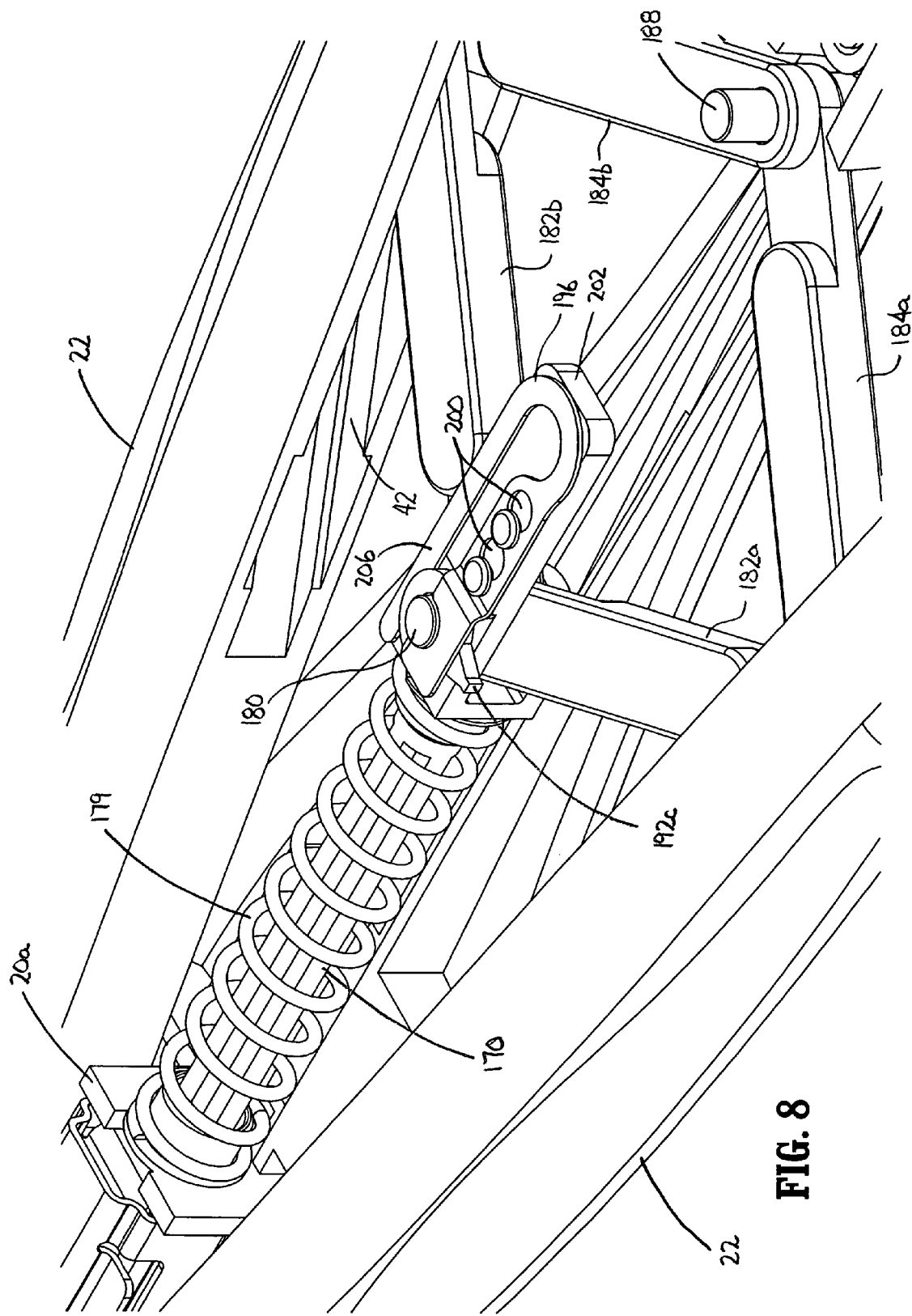
FIG. 8 is an enlarged view of the indicated area of detail shown in FIG. 6.

Embodiments of the presently disclosed surgical clip applier will now be described in detail with reference to the drawings wherein like reference numerals designate identical or corresponding elements in each of the several views. Throughout this description, the term "proximal" will refer to the portion of the instrument closest to the operator and the term "distal" will refer to the portion of the instrument furthest from the operator.

Referring to FIGS. 1-4, the presently disclosed surgical clip applier, shown generally as 10, includes a handle portion 12, an elongated body portion 14 extending distally from handle portion 12 and first and second jaws 16 and 18 which extend from the distal end of body portion 14. Briefly, handle portion 12 includes a handle housing 20 and a pair of movable handles or triggers 22. Each handle 22 includes a finger loop 22a for receiving a finger of a surgeon's hand.

Referring also to FIGS. 5-9, handle housing 20 can be formed from molded housing half-sections 20a and 20b (FIG. 5) which are secured together using screws 30 and nuts 32. Alternately, other fastening techniques may be used to secure housing half-sections 20a and 20b together, e.g., welding, rivets, interlocking structure, adhesives, etc. In one embodiment, the distal end of each handle 22 is pivotally secured about a pivot member 34 such that handles 22, when actuated, move in a scissor-like manner. Each pivot member 34 is positioned between recesses 36a and 36b formed in half-sections 20a and 20b, respectively, and may be formed integrally with a respective handle 22 or, in the alternative, as a separate element from a respective handle 22. In one embodiment, each handle 22 has a slip resistant grip member 40 secured to an outside surface thereof and a cam channel 42 formed on an inside surface thereof. Slip resistant grip member 40 can be formed from a cushioning material and overmolded onto each handle 22. It is also contemplated that other slip resistant materials and methods of application may be used to form grip member 40 and apply grip member 40 to a handle 22. Each cam channel 42 is configured to receive a pivot member for connecting a pair of pivotal links as will be described in more detail below.

Referring to FIG. 10, elongated body portion 14 includes a housing body 24 defining a channel 26 for receiving internal components of surgical clip applier 10. A housing cover 28 is secured to housing body 24 and covers channel 26. In one embodiment, housing cover 28 has a series of projections 50 which are dimensioned to be received within openings 52 formed along channel walls 26a of housing body 24 to secure housing cover 28 to housing body 24. Alternately, other securement techniques are contemplated, e.g., adhesives, crimping, screws, etc.

Referring also to FIGS. 13-15, an internal surface of housing cover 28 includes a first longitudinal groove 54 and a second longitudinal groove 56. Grooves 54 and 56 accommodate other components of the elongated body portion as will be discussed in further detail below. The distal end of housing cover 28 includes an outer surface 28a which is tapered or angled downwardly towards housing body 24. Angled outer surface 28a provides easier access to tissue and reduces the likelihood of the clip applier snagging tissue during use. An inner surface 28b formed on the distal end of housing cover 28 has a curvature which corresponds to the curvature of a top surface of jaws 16 and 18. Inner surface 28b is positioned in abutting relation to jaws 16 and 18 to provide stability to and prevent misalignment of jaws 16 and 18 during operation of clip applier 10.

Referring to FIGS. 10 and 21, housing body 24 includes a pair of distally located cutouts 60 configured to slidably receive jaws 16 and 18. Cutouts 60 are dimensioned to confine jaws 16 and 18 to prevent misalignment of the jaws during actuation of clip applier 10 (FIG. 30). The proximal end of housing body 24 includes a pair of transversely extending wings 62 which are dimensioned to be received within recesses 64 formed in housing half-sections 20a and 20b (FIG. 9) to secure elongated body portion 14 to handle portion 12.

Figure 23:
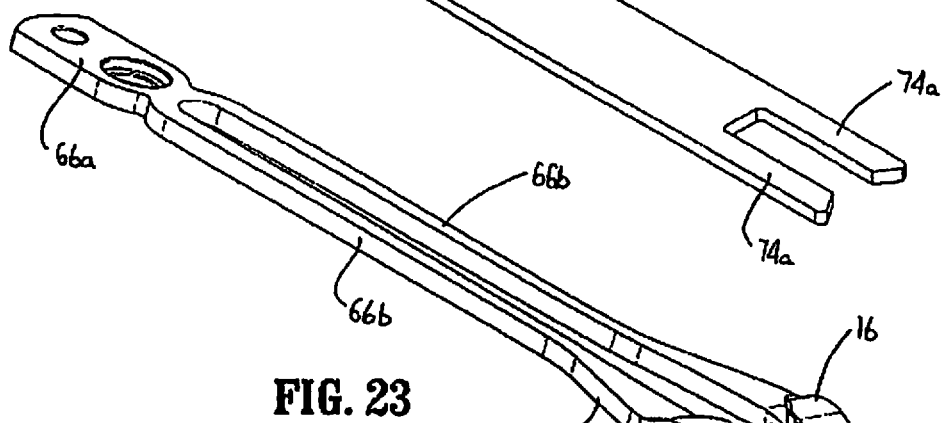
FIG. 23 is a top perspective view of the jaw body of the clip applying apparatus shown in FIG. 1.

As illustrated in FIG. 10, the internal components of clip applier 10 include a jaw body 66, a camming member 68, a clip pusher 70, a clip pusher lockout 72, a clip stack follower 74, and a clip stack 76 including a distal-most clip 76a and a proximal-most clip 76b. Referring also to FIG. 23, jaw body 66 includes jaws 16 and 18, a proximal mounting portion 66a and a pair of spaced distally extending legs 66b. Each of jaws 16 and 18 is supported on a distal end of a respective one of legs 66b and includes a clip channel 16a and 18a, respectively. A cam surface 70 is formed on an outer surface of each jaw 16 and 18. Cam surfaces 70 are positioned to be engaged by camming member 68 (FIG. 10) in a manner to be described in further detail below. Jaw body 66 is mounted within channel 26 of housing body 24 using a bolt 67 or the like. Bolt 67 extends through an opening 66d in body 66 and through housing body 24.

Figure 16:
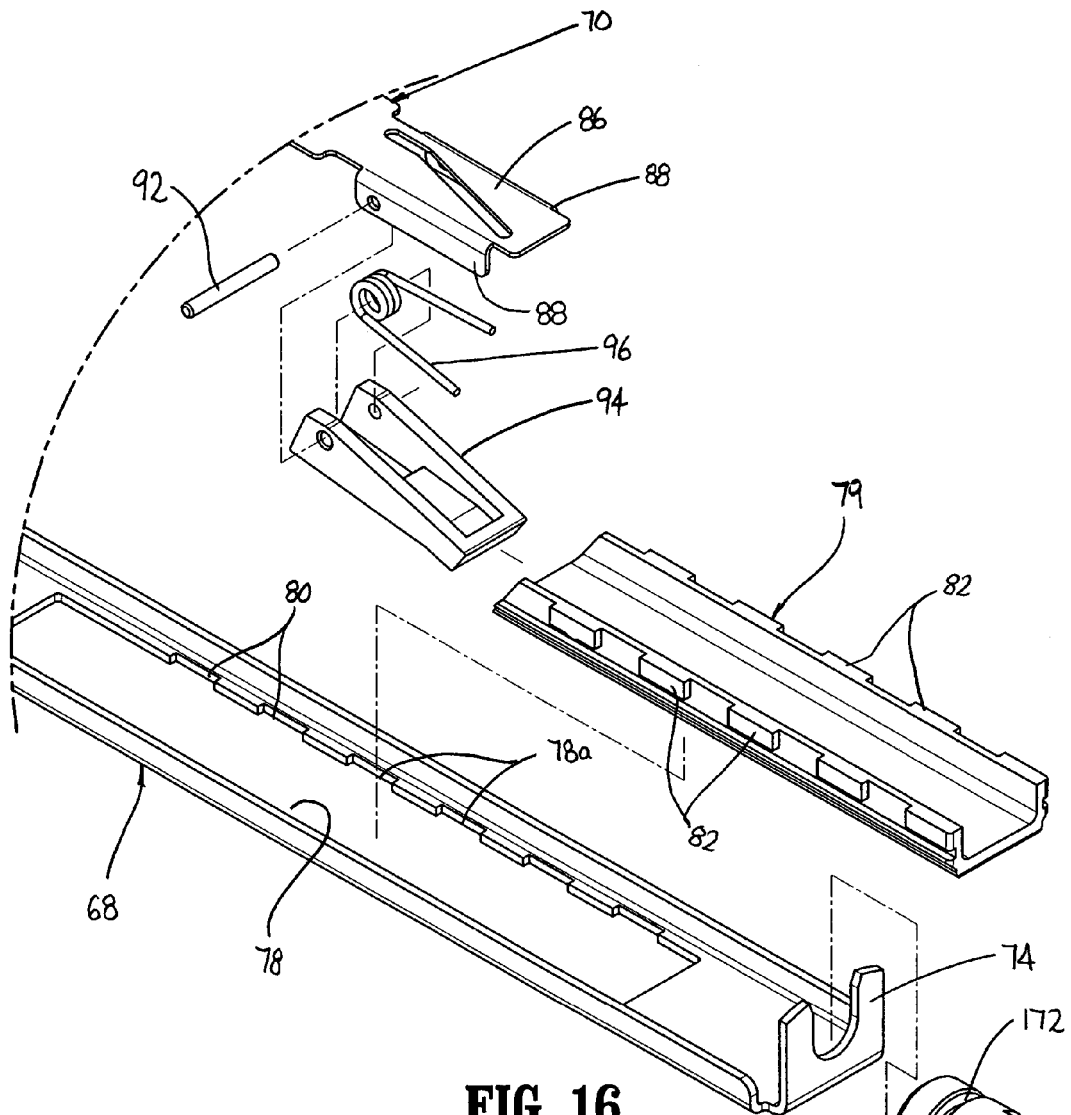
FIG. 16 is an enlarged view of the indicated area of detail shown in FIG. 10.
Figure 17:
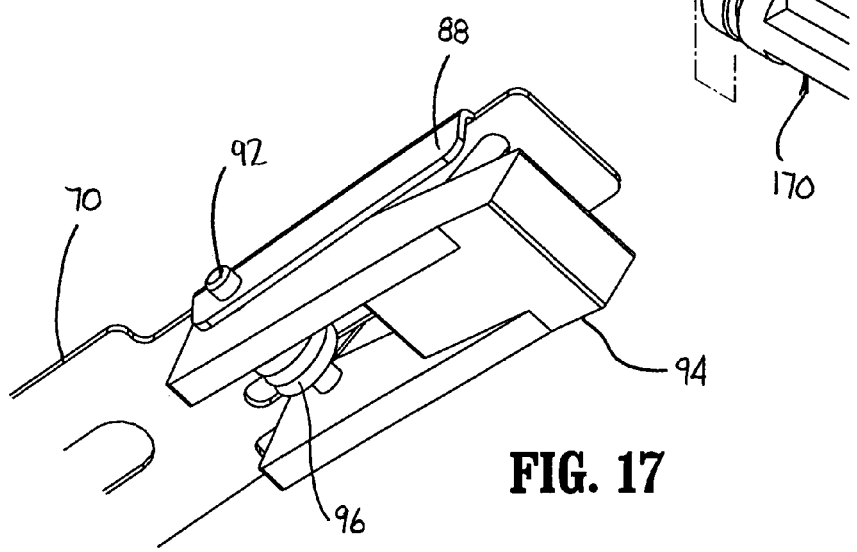
FIG. 17 is a perspective view of the proximal end of the clip pusher of the clip applying apparatus shown in FIG. 1 with the pusher latch assembly secured thereto.
Figure 46:
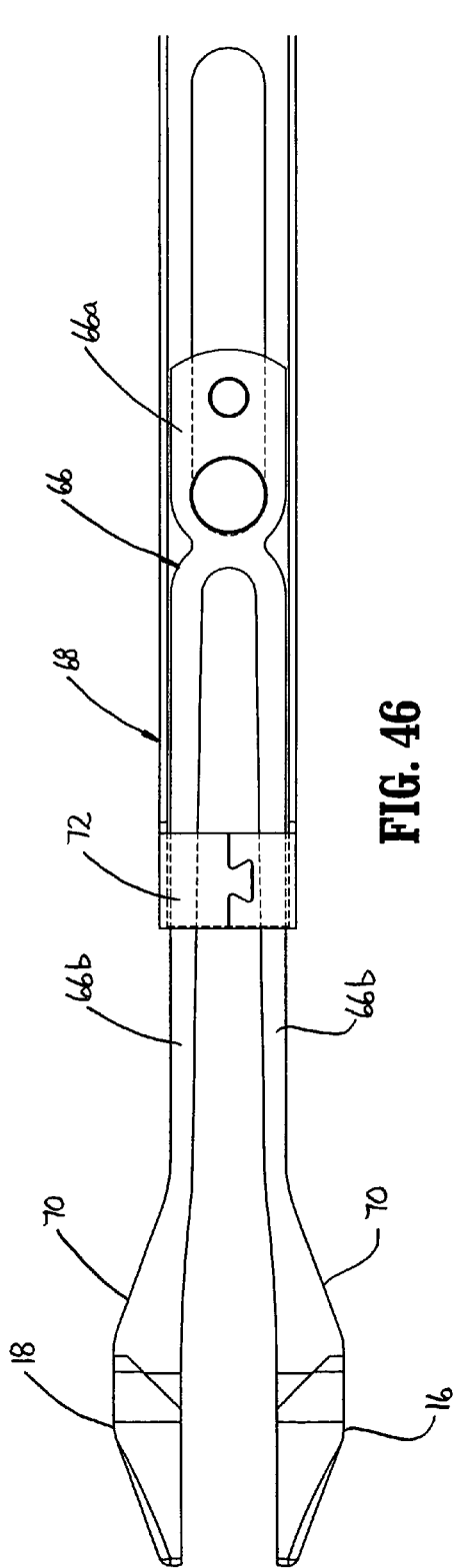
FIG. 46 is a top view of the jaw body and the distal end of the camming member of the clip applying apparatus shown in FIG. 36.
Figure 48:
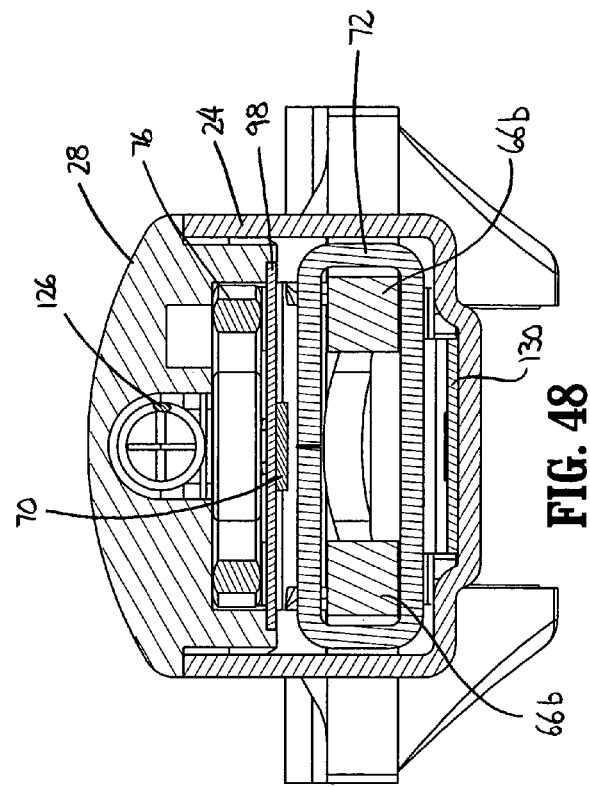
FIG. 48 is a cross-sectional view taken along section lines 48-48 of FIG. 40.
Figure 47:
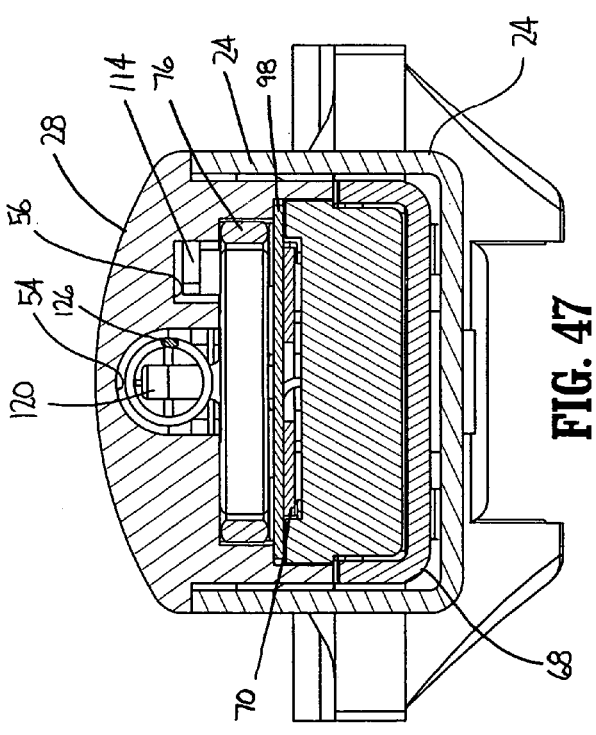
FIG. 47 is a cross-sectional view taken along section lines 47-47 of FIG. 44.
Figure 49:
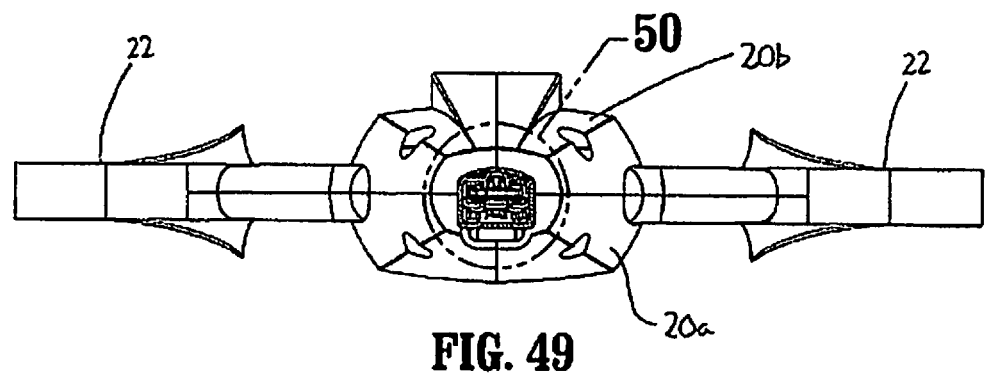
FIG. 49 is a cross-sectional view taken along section lines 49-49 of FIG. 42.
Figure 50:
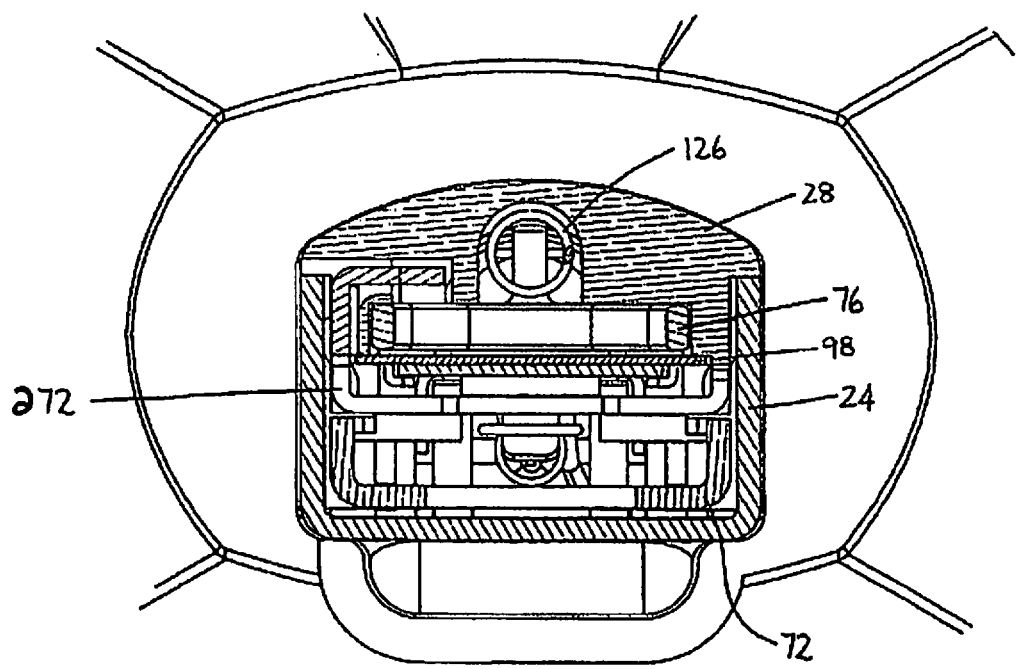
FIG. 50 is an enlarged view of the indicated area of detail shown in FIG. 49.

Referring now to FIGS. 10 and 16, camming member 68 is slidably supported within channel 26 (FIG. 10) of housing body 24 and includes a distal engagement member 72 which is positioned about legs 66b of jaw body 66 (FIG. 48). Engagement member 72 can have a substantially rectangular configuration. Alternately, other configurations are contemplated, e.g., C-shaped configuration. The proximal end of camming member 68 includes a bracket 74 to operably connect camming member 68 to handle portion 12 as will be discussed in further detail below. Handles 22 of handle portion 12 (FIG. 1) are operable to move camming member 68 between a retracted position and an advanced position along channel 26 of housing body 24. In the retracted position of camming member 68, engagement member 72 is positioned about legs 66b of jaw body 66 at a location proximal of cam surfaces 70 (FIG. 46). In the advanced position of camming member 68, engagement member 72 is positioned about jaws 16 and 18 in abutting relation to cam surfaces 70 (FIG. 60).

The proximal end of camming member 68 supports an abutment member 79. In one embodiment, abutment member 79 is supported within a cutout 78 formed in the proximal end of camming member 68. Cutout 78 includes a plurality of grooves 78a which receive tongues or projections 82 formed on abutment member 79 to secure abutment member 79 to camming member 68. It is contemplated that abutment member 79 may be attached to camming member 68 using other known fastening techniques. Alternately, abutment member 79 can be formed integrally with camming member 68. Abutment member 79 is positioned to engage a pusher latch assembly 80, as will be described in detail below.

Referring to FIGS. 10, 16, 17 and 20, clip pusher 70 includes an elongated body 82, a distal finger 84, and a proximal latch assembly mount 86. Distal finger 84 is semi-circular in shape and is positioned to engage distal-most clip 76a of the stack of clips 76 when clip pusher 70 is moved from a retracted position to an advanced position (FIG. 53). Latch assembly mount 86 includes a pair of spaced, vertical brackets 88. Brackets 88 each include an opening 90 for receiving a pivot pin 92 (FIG. 16) of pusher latch assembly 80.

Pusher latch assembly 80 includes a latch member 94, a biasing member 96, and pivot pin 92. Latch member 94 is pivotally secured at its distal end between brackets 88 of clip pusher 70 about pivot pin 92. Biasing member 96 is positioned between the proximal end of clip pusher 70 and latch member 94 to urge the proximal end of latch member 94 away from clip pusher 70 to a position to engage abutment member 79 when camming member 68 is moved from its retracted to its advanced position. Latch member 94 is pivotal against the urging of biasing member 96 towards the proximal end of clip pusher 70 to move latch member 94 out of engagement with abutment member 79 as will be discussed in further detail below.

Referring to FIGS. 10 and 18, a separator plate 98 is fixedly supported between housing body 24 and housing cover 28. Separator plate 98 includes a series of projections 100 which are received within recesses 102 formed in housing cover 28 to secure separator plate 98 to housing cover 28. The distal end of separator plate 98 includes a pair of spaced spring fingers 104 which are positioned to guide the distal-most clip 76a of clip stack 76 into jaws 16 and 18. A biasing member securement member 106 (FIG. 19) is formed on separator plate 98. A biasing member, which can be a coil spring 108, has one end secured to securement member 106 of separator plate 98 and a second end secured to a securement member 110 (FIG. 20) formed on clip pusher 70. Coil spring 108 is in tension and urges clip pusher 70 to its retracted position. When handles 22 (FIG. 1) are operated to move camming member 68 from its retracted position to its advanced position, abutment member 79 engages latch member 94 to move latch member 94 and clip pusher 70 distally toward its advanced position against the urging of coil spring 108. As clip pusher 70 moves distally with camming member 68, distal finger 82 of clip pusher 70 engages distal-most clip 76a of clip stack 76 to advance distal-most clip 76a into jaws 16 and 18.

Referring to FIGS. 10 and 12, a pusher latch cam 110 is supported in channel 26 between housing body 24 and housing cover 28. Pusher latch cam 110 includes a pair of tabs 110a which are received within recesses 112 formed in housing cover 28 to fixedly secure pusher latch cam 110 in relation to housing cover 28. Pusher latch cam 110 is positioned in channel 26 at a position to engage the distal end of latch member 94 (FIG. 57) to pivot and disengage latch member 94 from abutment member 79 when distal-most clip 76a has been fully advanced into jaws 16 and 18. When latch member 94 is disengaged from abutment member 79, coil spring 108 returns clip pusher 70 to its retracted position. Although pusher latch cam 110 is illustrated as block shaped, other configurations are envisioned. Further, pusher latch cam may be integrally formed with housing cover 28 or housing body 24.

Figure 22:
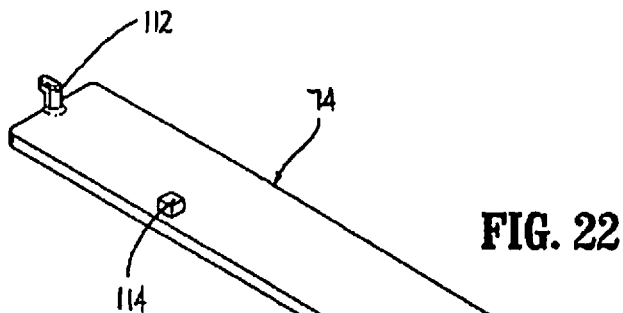
FIG. 22 is a top perspective view of the clip follower of the clip applying apparatus shown in FIG. 1.

Referring to FIGS. 10 and 22, clip stack 76 is slidably supported on a top surface of separator plate 98. A clip follower 74 is positioned behind the proximal-most clip 76b of clip stack 76. Clip follower 74 includes a pair of distally extending arms 74a. The distal end of each arm 74a is configured to engage the backspan of proximal-most clip 76b. A top surface of clip follower 74 includes a spring securement member 112 and a lockout tab 114. Lockout tab 114 is positioned to travel in second longitudinal groove 56 (FIG. 14) of housing cover 28 and is movable with clip follower 74 as clip follower 74 is advanced to move clip stack 76 distally within elongated body portion 14.

Figure 11:
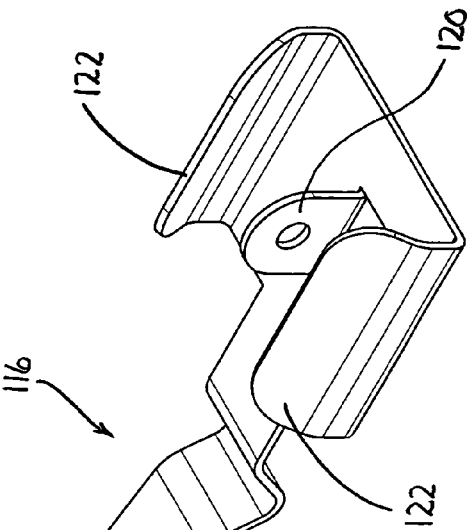
FIG. 11 is a perspective view of the clip stop member of the clip applying apparatus shown in FIG. 1.
Figure 9:
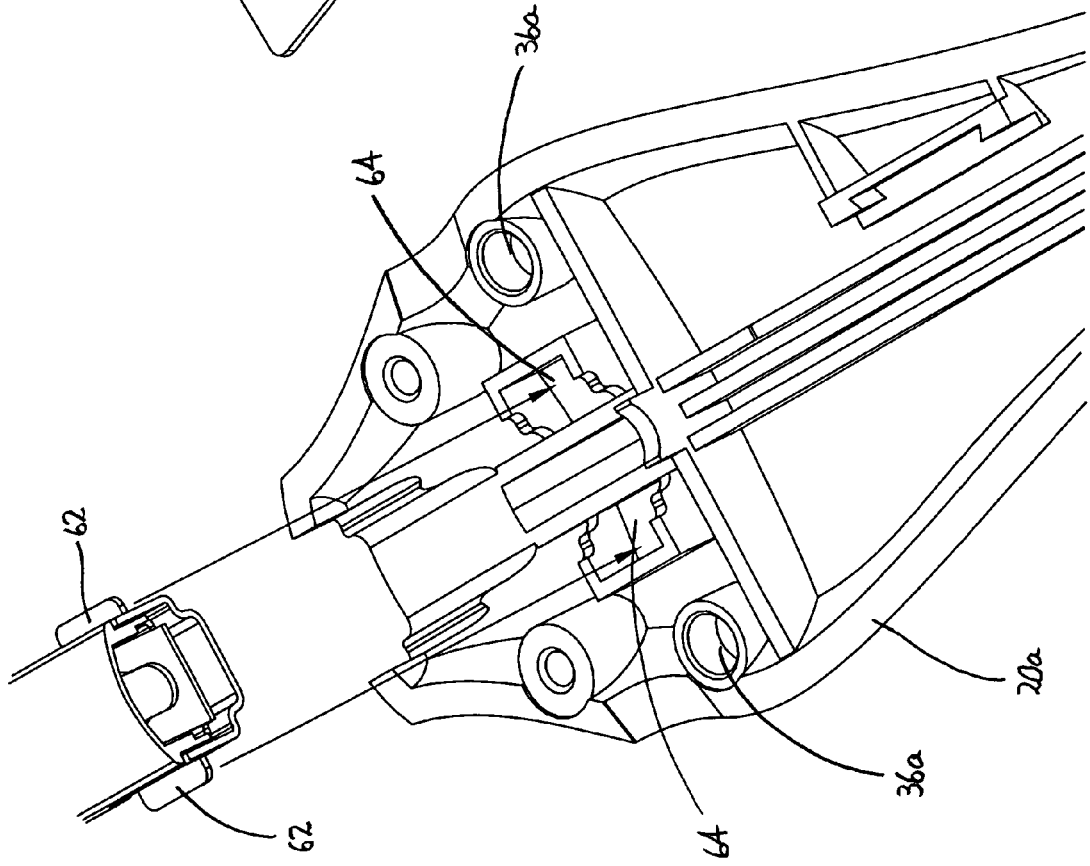
FIG. 9 is a perspective view of the proximal end of the body portion and the interior of a housing half-section with the internal components of the handle portion removed.

Referring to FIGS. 10 and 11, a clip stop member 116 includes a spring arm 118, a spring securement member 120 and a pair of anchor members 122. Anchor members 122 are dimensioned to be snap-fit into a pair of openings 124 formed through a distal portion of housing cover 28 to secure clip stop member 116 to the underside of housing cover 28. A biasing member 126 extends between spring securement member 120 of clip stop member 116 and spring securement member 112 of follower 74. Biasing member 126, which can be a coil spring, is supported in tension between follower 74 and clip stop member 116 to urge follower 74 and clip stack 76 distally within body portion 14 towards jaws 16 and 18. Biasing member 126 is positioned within first longitudinal groove 54 of housing cover 28 (FIG. 14). Clip stop member 116 prevents distal-most clip 76a from being pushed distally into jaws 16 and 18 until clip pusher 70 is moved to its advanced position. When clip pusher 70 is moved to its advanced position, clip stop member 116 is deflected upwardly by movement of distal-most clip 76a (FIG. 53).

Figure 59:
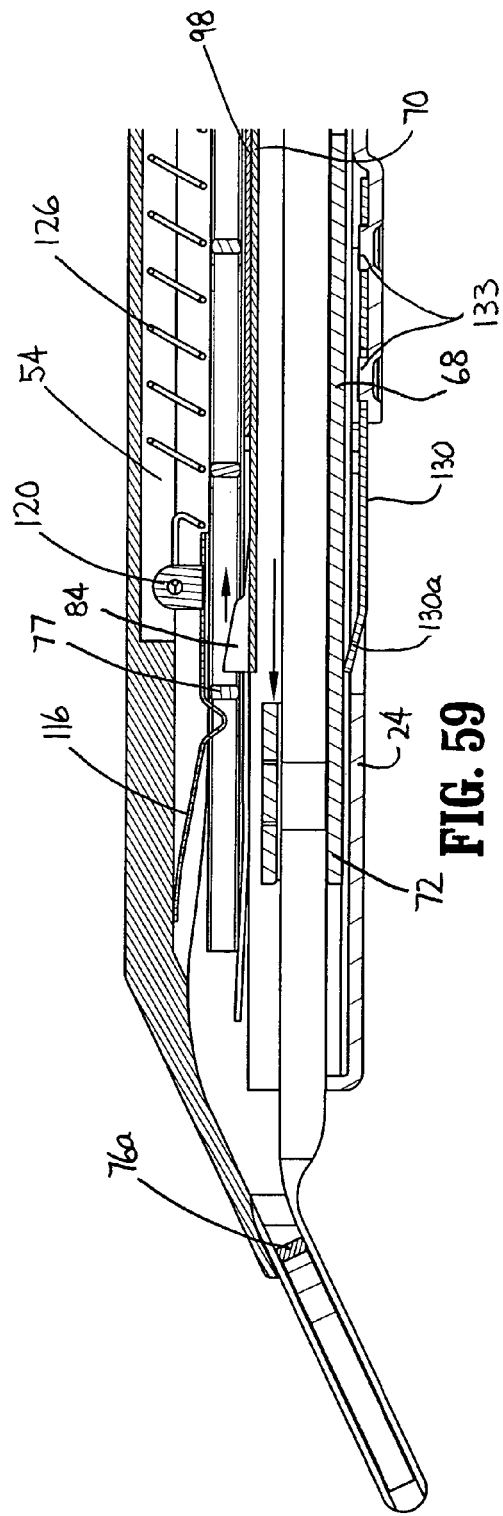
FIG. 59 is a side cross-sectional view of the distal end of the body portion shown in FIG. 55 after further actuation of the handle portion.

A jaw locking member, e.g., plate 130 (FIG. 10) is secured to housing body 24 within channel 26 of housing body 24. Jaw locking plate 130 includes openings 131 which are dimensioned to receive projections 133 (FIG. 59) formed on housing body 24 to secure plate 130 to body 24. Jaw locking plate 130 has a resilient and flexible arm 130a which is positioned between legs 66b of jaw body 66 to prevent jaws 16 and 18 from being closed inadvertently during positioning of clip applier 10 at a surgical site. When camming member 68 is moved to its advanced position, the distal end of engagement member 72 of camming member 68 deflects arm 130a downwardly to move arm 130a from between jaws 16 and 18 and allow for closure of jaws 16 and 18 (FIG. 59). Alternately, the jaw locking member need not be in the form of a flat plate but rather other configurations are envisioned, e.g., cylindrical or any configuration positionable between jaws 16 and 18 to prevent closure of the jaws.

Figure 24:
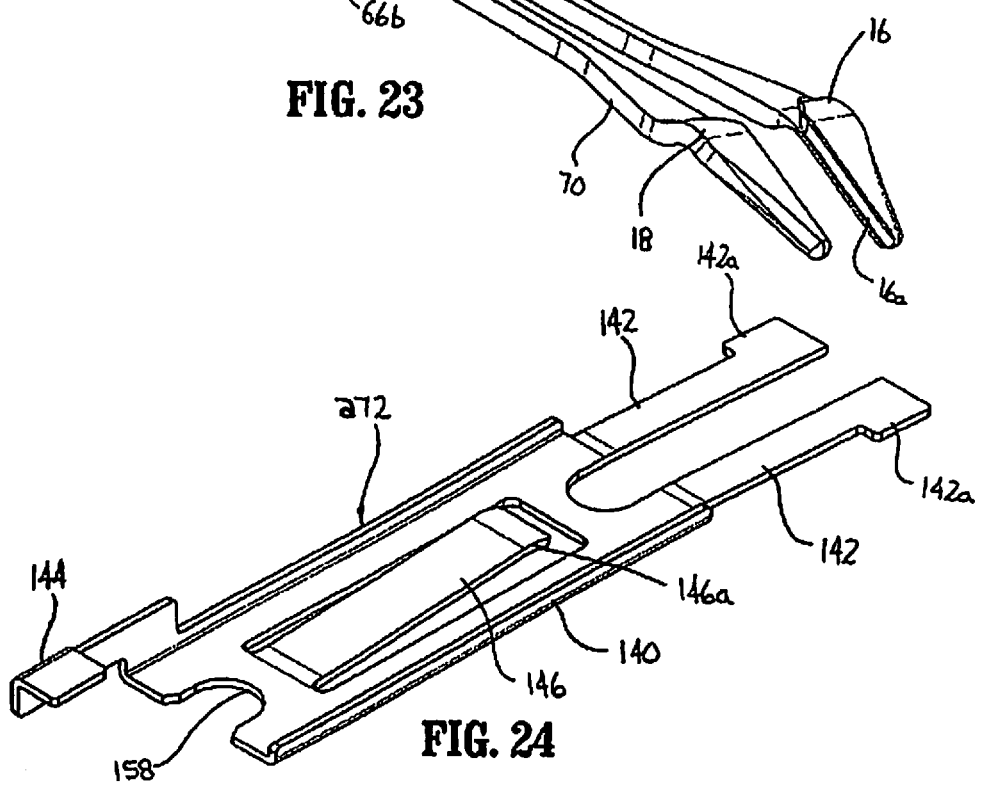
FIG. 24 is a top perspective view of the clip applying apparatus shown in FIG. 1.

Referring to FIGS. 10 and 24, a lockout member 272 is positioned above camming member 68 within channel 26 of housing body 24. Lockout member 272 includes a central body portion 140, a pair of flexible legs 142 and a distally extending engagement member or flag 144. Central body portion 140 includes a proximally extending resilient finger 146 which extends upwardly towards separator plate 98 and includes a downwardly curved end 146a. End 146a is positioned to extend through an elongated slot 148 formed in clip pusher 70 and to be partially received within an opening 150 formed in separator plate 98. Engagement of end 146a of finger 146 in opening 150 of separator plate 98 releasably retains lockout 272 at a fixed position in relation to separator plate 98 until an external force is applied to engagement member 144 as will be discussed in detail below.

Each of flexible legs 142 of lockout 272 includes a radial projection 142a. Legs 142 are positioned within the confines of sidewalls 152 of camming member 68 and are urged inwardly by sidewalls 152. A pair of slots 152a are formed in sidewalls 152 such that when projections 142a are moved into alignment with slots 152a, legs 142 spring outwardly to move radial projections 142a into slots 152a. When projections 142a are positioned within slots 152a, lockout 272 is fixedly secured to camming member 68.

As discussed above, follower 74 is urged distally by biasing member 126 to urge clip stack 76 distally along separator plate 98. As each clip 76a is advanced into jaws 16 and 18, follower 74 moves further distally within elongated body 14. As the proximal-most clip 76b is advanced in jaws 16 and 18, lockout tab 114 of follower 74 engages engagement member or flag 144 of lockout 272 and effects distal movement of lockout 272 in relation to camming member 68, such that after proximal-most clip 76b is crimped between jaws 16 and 18 and camming member 68 is returned to its retracted position, radial projections 142a align with slots 152a in camming member 68 to fixedly secure lockout 272 to camming member 68.

A stop member 156 (FIG. 10) is secured to a proximal end of mounting portion 66a of jaw body 66. In one embodiment, stop member 156 includes a cylindrical dowel. Alternately, other stop member configurations are envisioned. The distal end of lockout 272 includes a recess 158 for receiving stop member 156. Since stop member 156 is fixedly secured within channel 26 of housing body 24, engagement between lockout 272 and stop member 156 prevents further distal advancement of lockout 272. As discussed above, after the proximal-most clip 76b has been applied to tissue, lockout 272 is fixedly secured to camming member 68. Stop member 156 is also received in recess 158 of lockout 272. Thus, after proximal-most clip 76b has been applied to tissue and lockout 272 is fixed to camming member 86, engagement between lockout 272 and stop member 156 prevents distal advancement of camming member 68. As will be discussed below, since camming member 68 is connected via linkages to handles 22 (FIG. 1), engagement between lockout 272 and stop member 156 will prevent actuation of handles 22 and thus, indicate to a surgeon that the clip applier clip stack 76 has been depleted.

Figure 51:
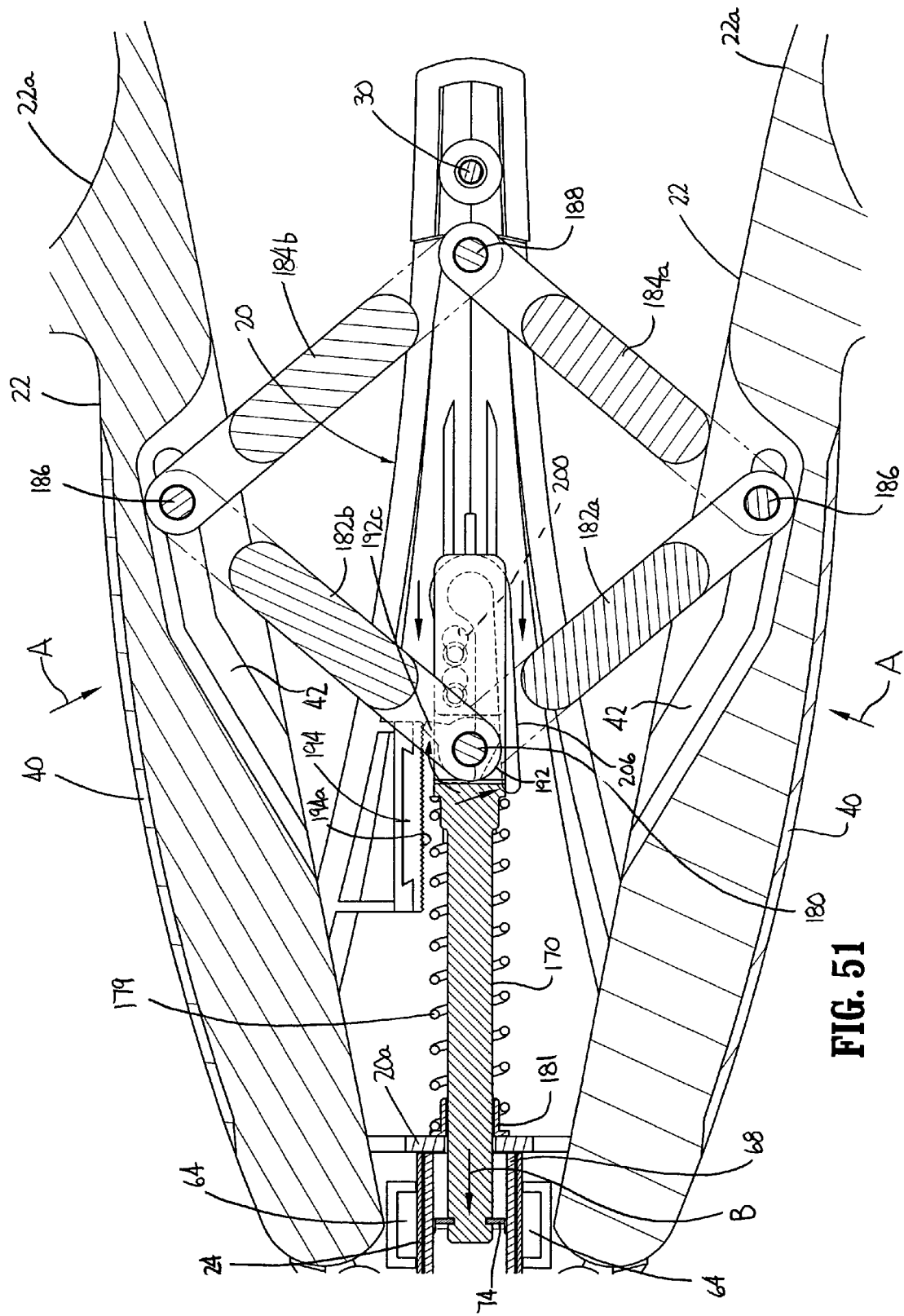
FIG. 51 is a top cross-sectional view of the handle portion of the clip applying apparatus shown in FIG. 1 during initial actuation of the handle portion.

Referring to FIGS. 5, 8, 25 and 28, handle portion 12 includes a yoke 170 which is slidably positioned between housing half-sections 20a and 20b between retracted and advanced positions. The distal end of yoke 170 includes an annular recess 172 which is dimensioned to be positioned in a semi-circular slot 174 (FIG. 16) formed in bracket 74 of camming member 68 to attach yoke 170 to camming member 68. The proximal end of yoke 170 includes a U-shaped connector 176 having a throughbore 178 dimensioned to receive a pivot pin 180. Pivot pin 180 pivotally connects yoke 170 to the distal end of front links 182a and 182b of a linkage assembly which connects handles 22 to yoke 170. The proximal end of front links 182a and 182b are pivotally secured to the distal end of rear links 184a and 184b, respectively, by pivot members 186. The proximal ends of rear links 184a and 184b are connected to each other and to handle housing 20 by a pivot member 188. Pivot member 188 is pivotally mounted between bores 190 formed in housing half-sections 20a and 20b (FIG. 5). Pivot members 186 are received within a respective cam channel 42 formed in a respective handle 22. When handles 22 are actuated, i.e., moved towards housing 20, pivot members 186 are caused to move through cam channels 42 such that front links 182a, 182b and rear links 184a, 184b are moved from a first misaligned position towards an aligned position (FIG. 51). Since the proximal end of rear links 184a and 184b are axially fixed between housing half-sections 20a and 20b, movement of front links 182a and 182b and rear links 184a and 184b toward an aligned position moves the distal end of front links 182a and 182b distally within housing 20. As discussed above, the distal end of front links 182a and 182b is axially fixed to yoke 170 by pivot member 180. As such, when handles 22 are actuated, yoke 170 is moved distally to move camming member 68 distally. A biasing member, e.g., coil spring 179, is positioned about a distal end of yoke 170 and abuts a spring stop 181 supported within housing 20 to urge yoke 170 to its retracted position.

Figure 25:
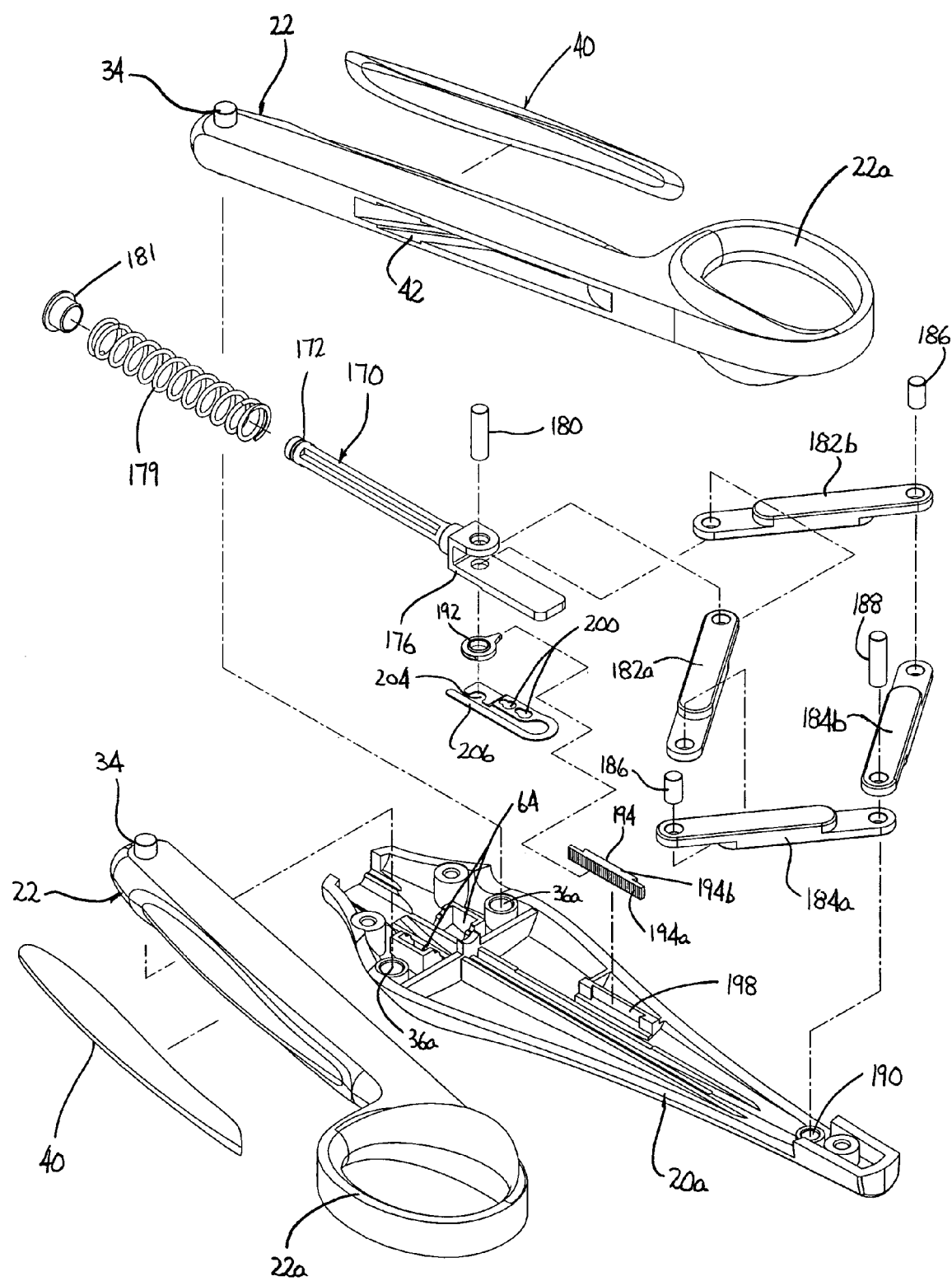
FIG. 25 is an exploded perspective view of the handle portion of the clip applying apparatus shown in FIG. 1.
Figure 26:
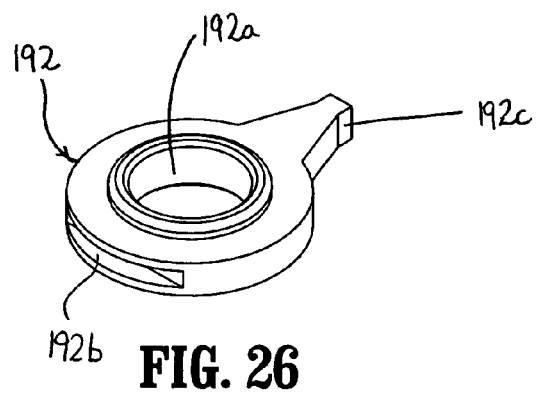
FIG. 26 is a perspective view of the pawl of the handle portion shown in FIG. 25.
Figure 27:
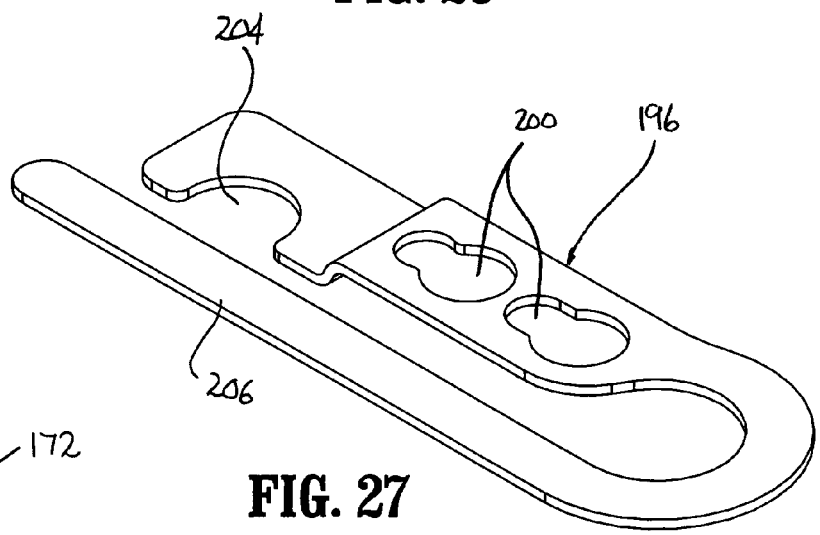
FIG. 27 is a perspective view of the pawl biasing member of the handle portion shown in FIG. 25.
Figure 28:
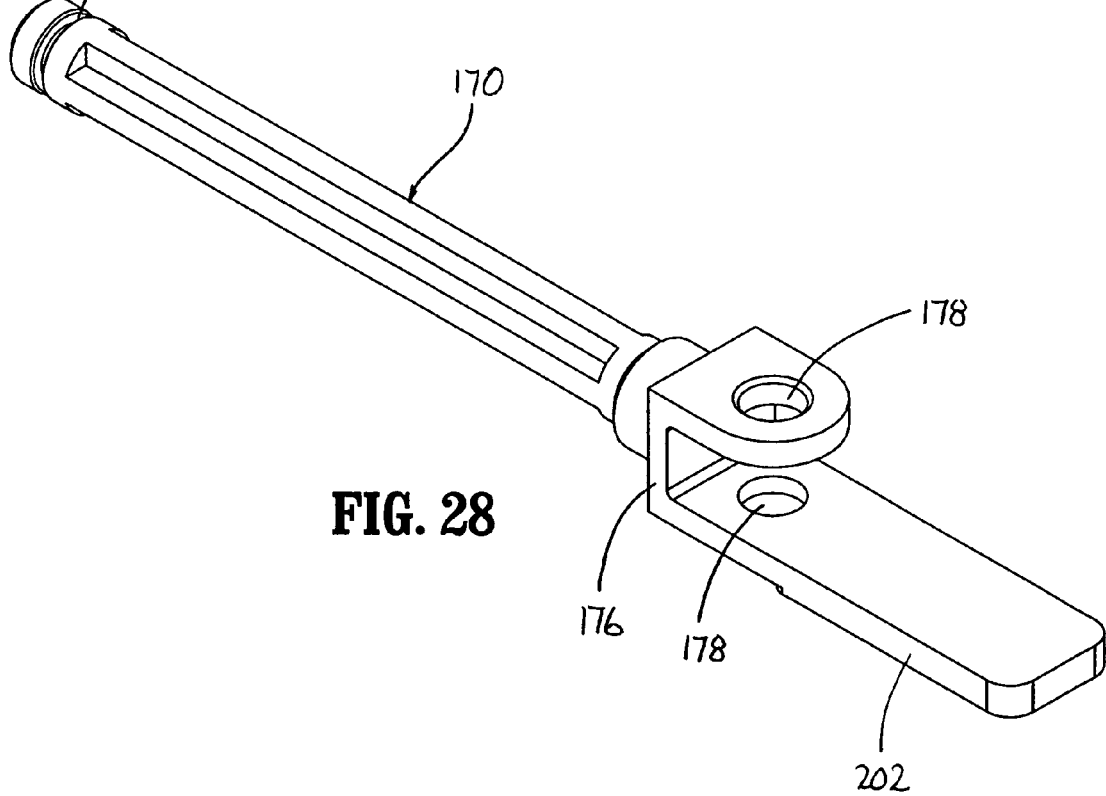
FIG. 28 is a perspective view of the yoke of the handle portion shown in FIG. 25.

Referring to FIGS. 25-27, handle portion 12 includes an anti-reverse ratchet mechanism which includes a pawl 192, a rack 194, and a pawl biasing member 196. Rack 194 includes a series of teeth 194a and is supported within a recess 198 formed in housing half-section 20a. In one embodiment, recess 198 is dovetail shaped and the backside of rack 194 has a dovetail shape projection 194b which is slidably received within recess 198 to secure rack 194 within housing 20. Alternately, other fastening techniques can be used to secure rack 194 within housing 20, e.g., adhesives, pins, welding, etc.

Pawl 192 includes a bore 192a dimensioned to receive pivot member 180 such that pawl 192 is rotatably mounted to yoke 170 about pivot member 180. Pawl biasing member 196 includes a pair of mounting holes 200 for securing bracket 196 to a plate extension 202 (FIG. 28) of yoke 170. Pawl biasing member 196 also includes a semi-circular cutout 204 which is positioned to be clipped partially about pivot member 180, and a cantilever or spring arm 206 which is positioned within a slot 192b formed in a backside of pawl 192. Cantilever arm 206 is resilient and provides a biasing force to urge pawl 192 to a position in which pawl finger 192c is substantially perpendicular to arm 206. Finger 192c is positioned to engage teeth 194a of rack 194 to retain yoke 170 at partially advanced positions during actuation of clip applier 10 against the bias of spring 179 which urges yoke 170 to its retracted position. The anti-reverse ratchet mechanism prevents retraction of yoke 170 and camming member 68 after handles 22 have been partially actuated until the clip applier has been fully actuated.

Figures 36, 37:
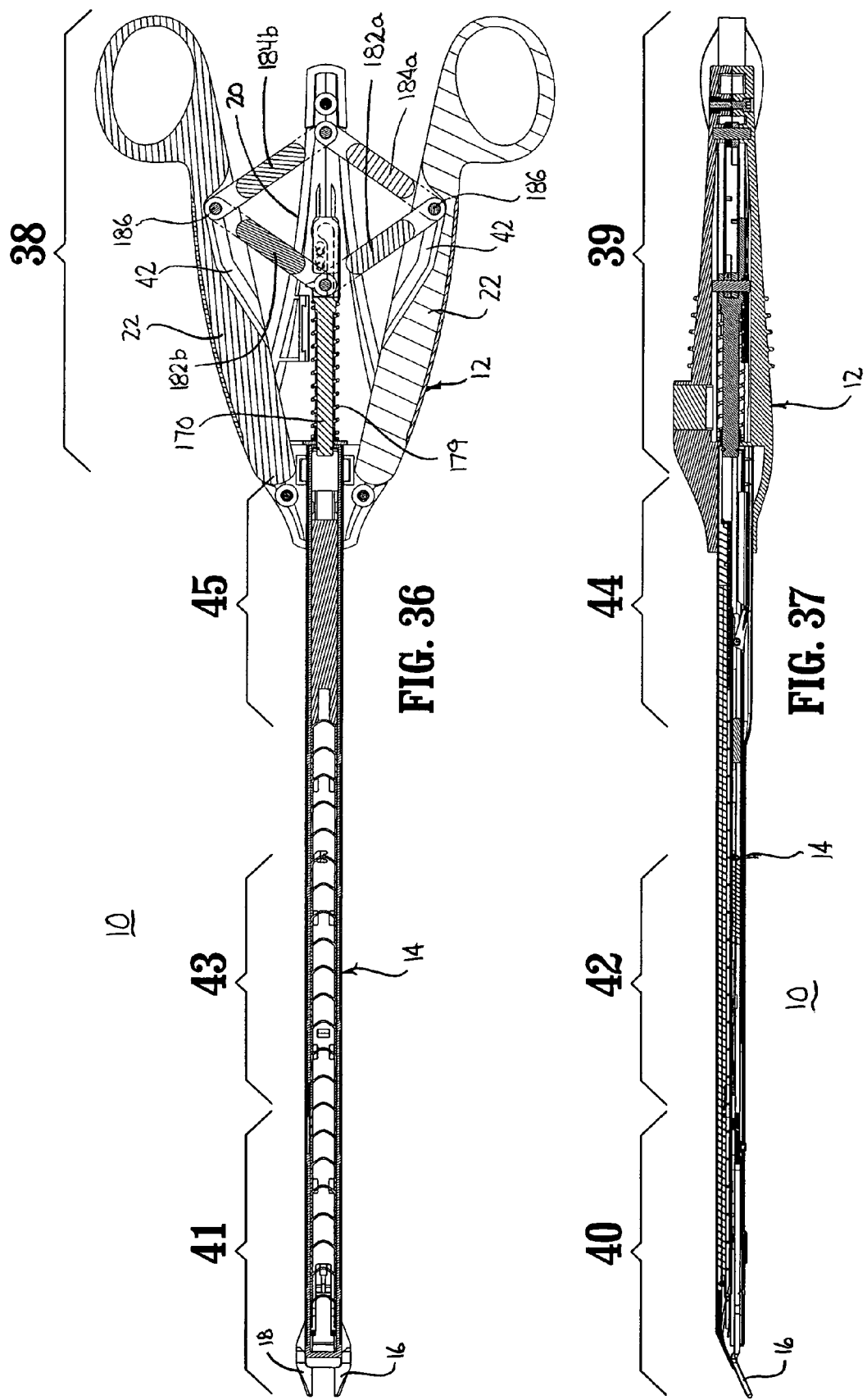
FIG. 36 is a top cross-sectional view of the clip applying apparatus shown in FIG. 1 prior to actuation of the apparatus.
FIG. 37 is a side cross-sectional view of the clip applying apparatus shown in FIG. 36.

Referring to FIGS. 36-67, operation of clip applier 10 will now be described. FIGS. 36-50 illustrate clip applier 10 prior to actuation of handles 22, i.e., in the prefired position. In the prefired position, biasing member 179 urges yoke 170 to its retracted position. When yoke 170 is in its retracted position, pivot members 186 are positioned within cam channels 42 (FIG. 36) such that front links 182a and 182b and rear links 184a and 184b are in their misaligned position, handles 22 are spaced from housing 20 of clip applier 10, and pawl 192 (FIG. 38) is positioned proximally of rack 194 (FIG. 38). Referring to FIGS. 40-50, in the prefired position, caroming member 68 is urged to its retracted position by yoke 170 and biasing member 179 (FIG. 39). Clip pusher 70 is urged to its retracted position by biasing member 108 (FIG. 42). Clip stack 76 is urged by follower 74 (FIG. 44) and biasing member 126 distally within body 14, but distal-most clip 76a is prevented from moving into jaws 16 and 18 by spring arm 118 of clip stop member 116 (FIG. 40). Jaw locking plate 130 is positioned between jaw legs 66b to prevent inadvertent closure of jaws 16 and 18 (FIG. 40). It is also noted that latch member 94 of pusher latch assembly 80 is spaced distally of but in a position to engage abutment member 79 which is supported on caroming member 68 (FIG. 44). Further, radial projections 142a of lockout 272 are positioned proximally of slots 152a of caroming member 68 and recess 158 of lockout 272 is positioned proximally of stop member 156.

FIGS. 51-63 illustrate clip applier 10 in various stages of operation. Referring to FIG. 51, handles 22 have been partially actuated or moved towards housing 20 in the direction indicated by arrow "A". Actuation of handles 22 moves front links 182a and 182b towards their aligned position to advance yoke 170 distally in the direction indicated by arrow "B". Referring to FIG. 52, as yoke 170 is advanced, camming member 68 which is secured to yoke 170 is advanced distally within elongated body 14 of clip applier 10. Abutment member 79 is supported on camming member 68 and is also advanced distally within elongated body 14 in the direction indicated by arrow "C". During the initial actuation stroke of handles 22, abutment member 79 engages latch member 94 of pusher latch assembly 80 to effect advancement of clip pusher 70 in the direction indicated by arrow "D". Referring to FIG. 53, as clip pusher 70 advances, engagement finger 84 of clip pusher 70 advances distal-most clip 76a of clip stack 76 past spring arm 118 of clip stop member 116 into jaws 16 and 18. As the distal-most clip 76a of clip stack 76 is advanced into the jaws, follower 74 (FIG. 52) under the force of biasing member 126 advances clip stack 76 distally in the direction indicated by arrow "E" in FIG. 53 to position the second distal-most clip 77 adjacent clip stop member 116 (See FIGS. 53-55).

Figure 58:
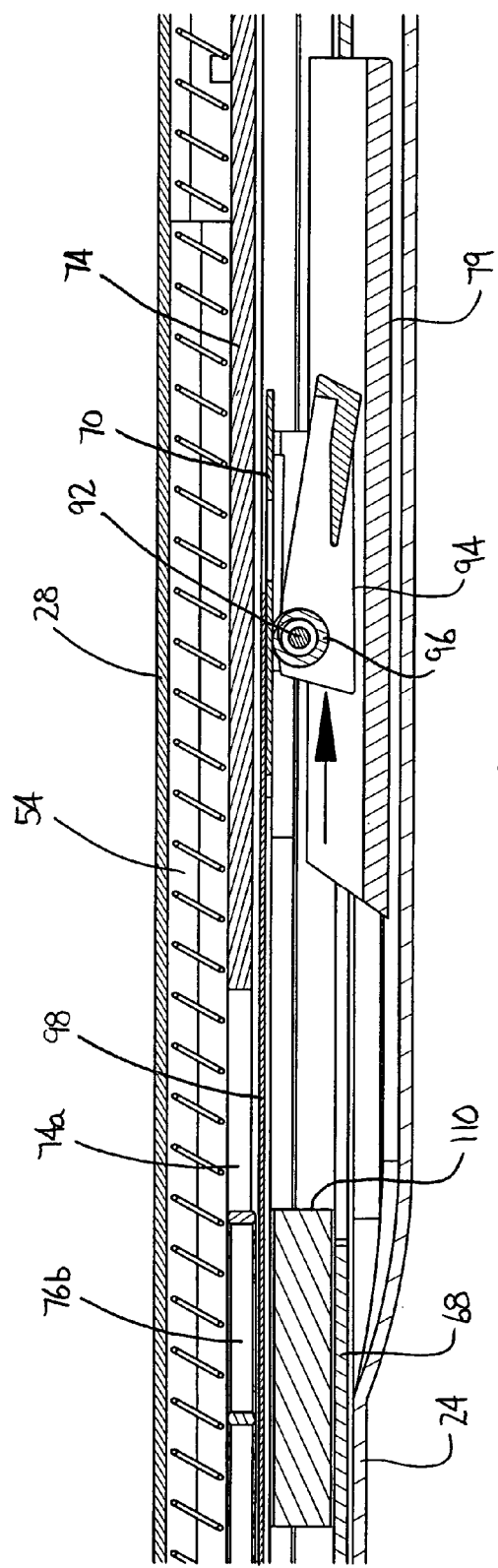
FIG. 58 is a side cross-sectional view of the body portion shown in FIG. 57 after further actuation of the handle portion.

Referring to FIGS. 55-57, as camming member 68 and clip pusher 70 advance within elongated body 14, the tension in spring 108 is increased, i.e., spring 108 is stretched (FIG. 56). When distal-most clip 76a is fully positioned within jaws 16 and 18, pusher latch cam 110 engages a distal end of latch member 94 and pivots latch member 94 in the direction indicated by arrow "F" against the urging of biasing member 96 to release latch member 94 from abutment member 79. When latch member 94 is released from abutment member 79, biasing member 108 returns clip pusher 70 to its retracted position (FIGS. 58 and 59).

As handles 22 are more fully actuated, i.e., moved closer to housing 20, camming member 68 engages finger 130a of jaw locking plate 130 (FIG. 55) to deform plate 130 downwardly from between legs 66b of jaw body 66. Continued advancement of camming member 68 advances engagement member 72 into camming surfaces 70 of jaws 16 and 18 to move jaws 16 and 18 from a spaced position (FIG. 46) to a crimping position (FIG. 63).

Referring to FIG. 51, as yoke 170 is moved from its retracted position within housing 20 to its advanced position, a finger 192c of pawl 192 engages teeth 194a of rack 194 to prevent spring 179 from returning yoke 170 to its retracted position when handles 22 are released. As such, once handles 22 begin to be actuated and pawl 192 engages rack 194 (FIG. 51) yoke 170 cannot be returned to its retracted position until clip applier 10 is fully actuated. When yoke 170 is moved to its advanced position, pawl 192 passes by the distal end of rack 194 (FIG. 61) and cantilevered or spring arm 206 of pawl biasing member 196 will rotate pawl 192 in the direction indicated by arrow "G" in FIG. 61 to a position in which finger 192a of pawl 192 is positioned at 12:00. Thus, when handles 22 are released and spring 179 returns yoke 170 to its retracted positioned (FIG. 64) finger 192c will engage the distal end of rack 194 and rotate counter-clockwise in the direction indicated by arrow "H" in FIG. 64 and ratchet over teeth 194a of rack 194. Note, in the fully retracted position of yoke 170, pawl 192 is positioned proximally of rack 194. In this position cantilevered arm 206 (FIG. 61) returns finger 192c of pawl 192 to the 12:00 position.

Figure 62:
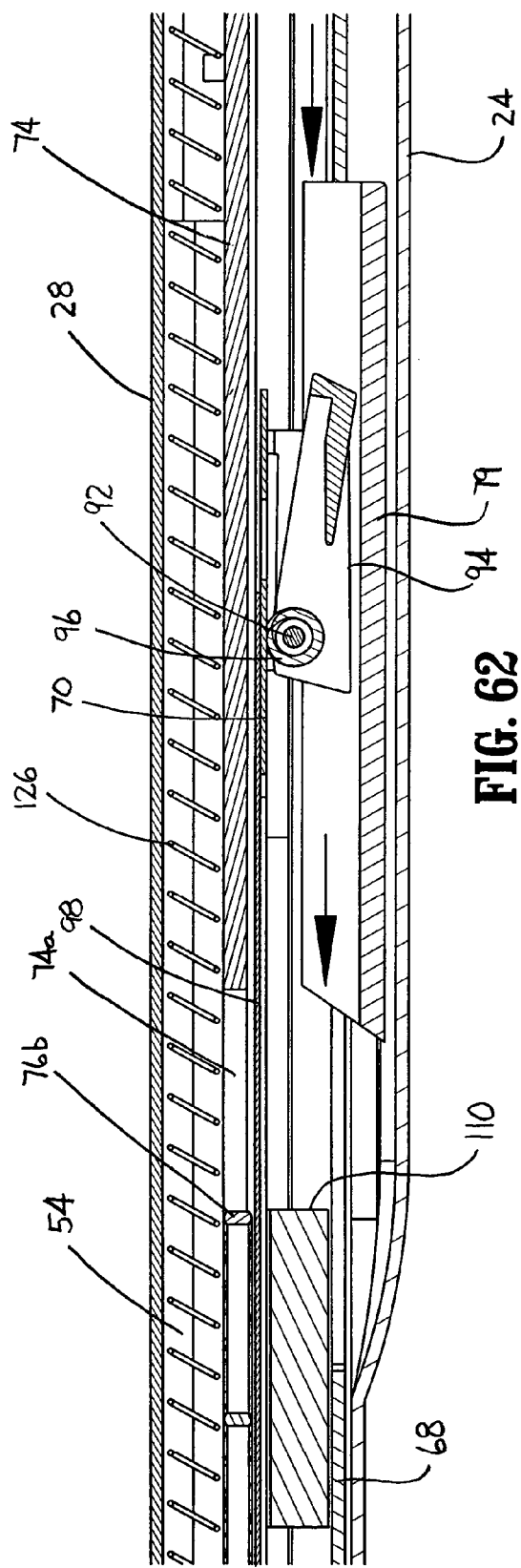
FIG. 62 is a side cross-sectional view of the body portion shown in FIG. 58 after further actuation of the handle portion.
Figure 63:
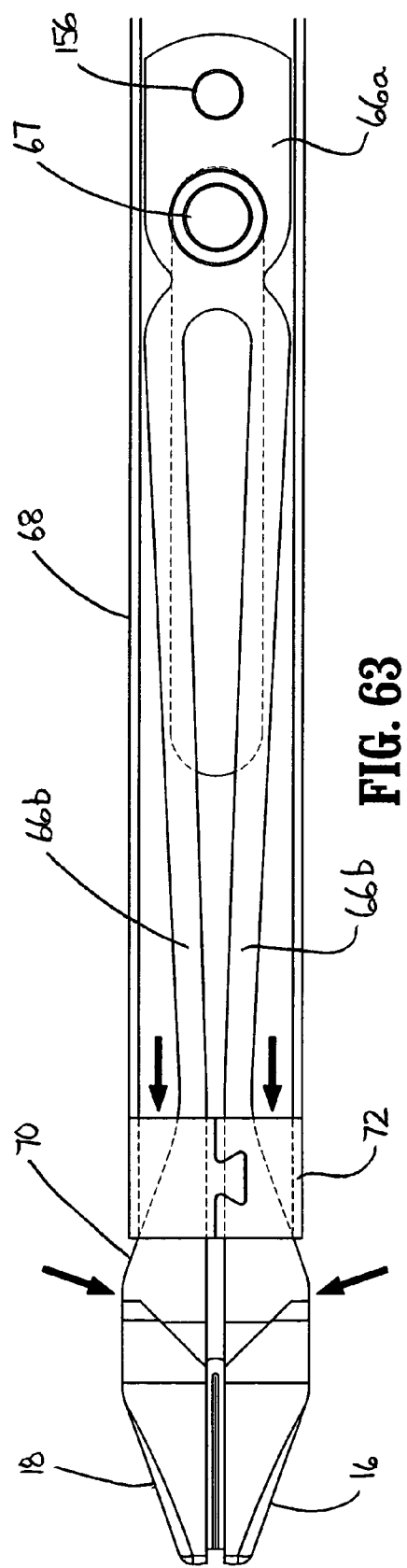
FIG. 63 is a top view of the jaw body and camming member shown in FIG. 60 with camming member fully advanced.
Figure 64:
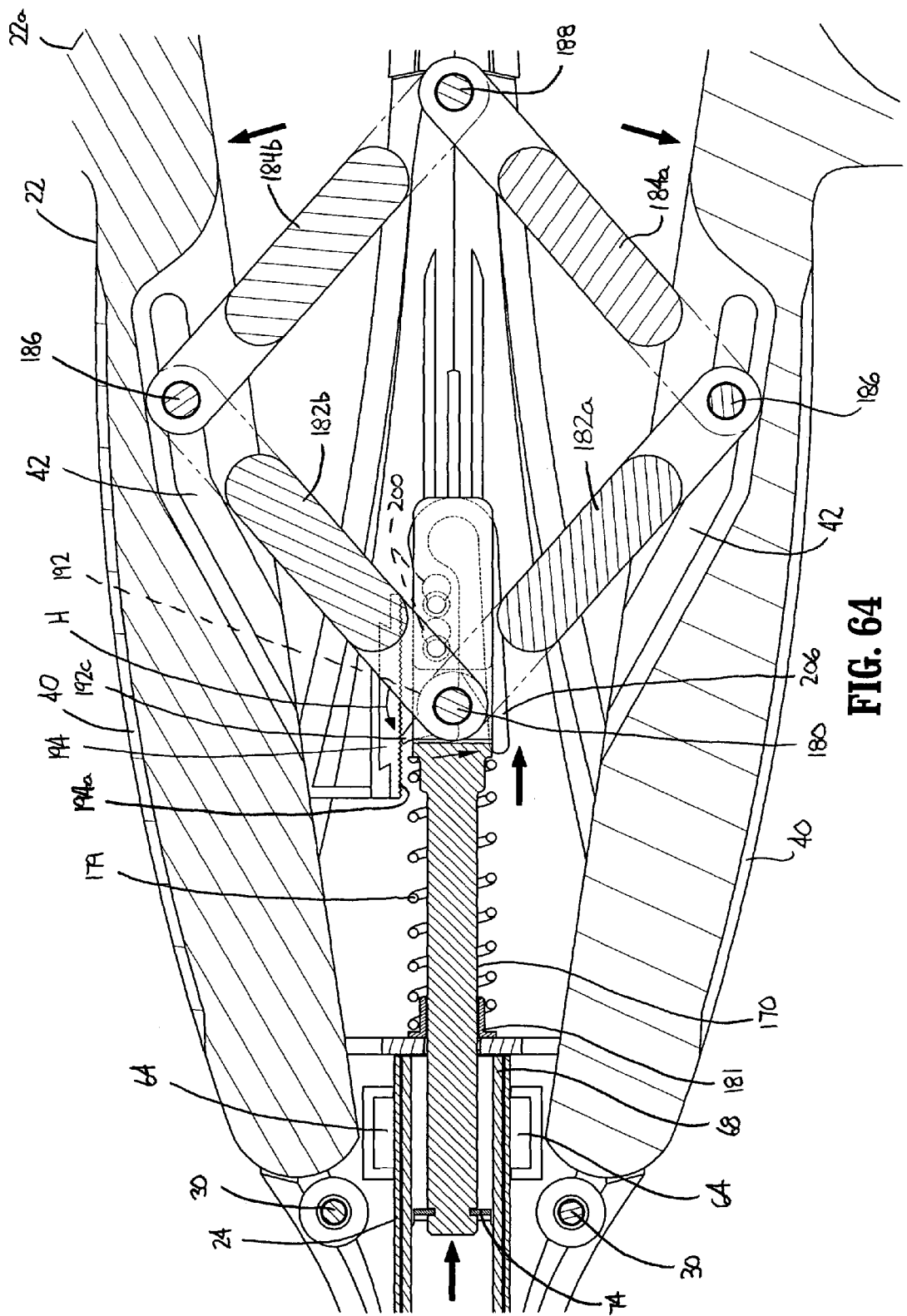
FIG. 64 is a top cross-section view of the handle portion shown in FIG. 61 after the handle portion has been returned to the unactuated position.

After the device has been fully actuated as shown in FIGS. 61-63 and handles 22 have been released, yoke 170 is moved to its retracted position by spring 179. Camming member 68, which is secured to yoke 170, is also moved toward its retracted position. As this occurs, resilient jaws 16 and 18 return to their spaced position and camming member 68 moves past jaw locking plate 130 allowing locking plate finger 130a to return to a position located between legs 66b of jaw body 66. As discussed above, the positioning of locking plate 130 between legs 66b of jaw body 66 prevents inadvertent closure of jaws 16 and 18.

Referring to FIGS. 65 and 66, after the proximal-most clip 76b has been advanced beyond clip stop member 116, clip follower 74 is advanced towards its fully advanced position by biasing member 126. As this occurs, lockout tab 114 formed on follower 74 engages engagement member 144 of lockout 272 to advance lockout 272 distally in relation to camming member 68 to move radial projections 142a of flexible legs 142 of lockout 272 into slots 152a of camming member 68 and secure or interlock lockout 272 to camming member 68. When lockout 272 is moved distally within elongated body 14 by follower 74, distal recess 158 of lockout 272 receives stop member 156, which is secured to mounting portion 66a of jaw body 66 such that the distal end of lockout 272 engages stop member 156. Engagement between the distal end of lockout 272 and stop member 156 prevents further distal movement of lockout 272 and, thus, camming member 68.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:
1. An apparatus for applying surgical clips comprising:
   a body portion housing a clip stack; and
   a pair of jaws supported at a distal end of the body portion;
   the body portion including a clip pusher, a camming member and a clip follower, the clip pusher being movably positioned within the body portion and being operable to advance a distal-most clip from the clip stack to a position between the pair of jaws, the camming member being movably positioned within the body portion and being operable to approximate the pair of jaws in response to direct engagement with the pair of jaws to deform the distal-most clip resulting from a distal movement of the camming member, and the clip follower being positioned proximally of the clip stack and operable to urge the clip stack distally towards the pair of jaws;

wherein the body portion further includes a lockout member and a stop member, the lockout member including a central body portion defining a recess in a distal end of the central body portion, the lockout member being movable from a first position in slidable relation to the caroming member to a second position interlocked with the camming member such that the lockout member and the camming member move in unison with one another, wherein in its second position, the recess of the lockout member abuts the stop member to limit distal movement of the camming member.

2. The apparatus according to claim 1, wherein the lockout member includes at least one flexible leg having a projection and the camming member includes at least one slot dimensioned to receive the projection to interlock the lockout member to the camming member.

3. The apparatus according to claim 2, wherein the at least one flexible leg includes a pair of flexible legs and the at least one slot includes a pair of slots.

4. The apparatus according to claim 2, wherein the clip follower includes a tab and the lockout member includes an engagement member that extends distally from a distal end of the lockout member, the tab being movable into the engagement member to move the lockout member from its first position to its second position.

5. The apparatus according to claim 4, wherein when the lockout member is disposed in the second position, the lockout member and the camming member are positioned to simultaneously move distally until a recess defined in the lockout abuts the stop member to prevent further distal movement of lockout and camming member.

6. The apparatus according to claim 1, wherein the lockout member includes a resilient finger which is positioned to releasably retain the lockout member in its first position.

7. The apparatus according to claim 6, wherein the body portion further includes a separator plate, the separator plate including an opening dimensioned to receive a portion of the resilient finger of the lockout member.

8. The apparatus according to claim 1, wherein the clip follower includes a tab and the lockout member includes an engagement member, the tab being movable into the engagement member to move the lockout member from its first position to its second position.

9. The apparatus according to claim 8, wherein the tab is positioned to engage the engagement member after the proximal most clip has been advanced to the pair of jaws.

10. The apparatus according to claim 8, wherein the engagement member extends distally from a distal end of the lockout member.

11. The apparatus according to claim 1, wherein the lockout member includes at least one flexible leg having a projection, the camming member includes at least one slot, and the clip follower includes at least one tab that is movable into an engagement member that extends distally from a central body portion of the lockout member, wherein engagement of the at least one tab with the engagement member moves the lockout member to the second position so that the projection of the at least one flexible leg is received by the at least one slot of the camming member to interlock the lockout member to the camming member.

12. The apparatus according to claim 1, wherein the lockout member defines a plane in the first position, the lockout member being movable along and remaining within the plane as the lockout member moves from the first position to the second position.

* * * * *